(12) United States Patent
Peakman et al.

(10) Patent No.: US 7,408,031 B2
(45) Date of Patent: Aug. 5, 2008

(54) PEPTIDE EPITOPES RECOGNIZED BY DISEASE PROMOTING CD4+ T LYMPHOCYTES

(75) Inventors: Mark Peakman, London (GB); Roman M. Chicz, Belmont, MA (US)

(73) Assignees: MGI PHARMA Biologics, Inc., Lexington, MA (US); King's College London, London (GB)

( * ) Notice: Subject to any disclaimer, the term of this patent is extended or adjusted under 35 U.S.C. 154(b) by 0 days.

(21) Appl. No.: 11/670,830

(22) Filed: Feb. 2, 2007

(65) Prior Publication Data

US 2007/0135618 A1  Jun. 14, 2007

Related U.S. Application Data

(62) Division of application No. 10/378,479, filed on Mar. 3, 2003, now Pat. No. 7,173,108, which is a division of application No. 09/552,802, filed on Apr. 20, 2000, now Pat. No. 6,562,943.

(60) Provisional application No. 60/130,355, filed on Apr. 21, 1999.

(51) Int. Cl.
*C07K 4/12* (2006.01)
*C07K 14/00* (2006.01)

(52) U.S. Cl. ........................ 530/329; 530/324; 530/325; 530/326; 530/327; 530/328

(58) Field of Classification Search ........................ None
See application file for complete search history.

(56) References Cited

U.S. PATENT DOCUMENTS 5,827,516 A  10/1998  Urban et al.

FOREIGN PATENT DOCUMENTS

WO   WO 94/04171   3/1994
WO   WO 99/55849   11/1999

OTHER PUBLICATIONS

Atkinson et al., "64 000 Mr autoantibodies as predictors of insulin-dependent diabetes," The Lancet 335:1357-60, 1990.
Atkinson et al., "Cellular Immunity to a Determinant Common to Glutamate Decarboxylase and Coxsackie Virus in Insulin-dependent Diabetes," J. Clin. Invest. 94:2125-2129, 1994.
Atkinson et al., "Response of peripheral-blood mononuclear cells to glutamate decarboxylase in insulin-dependent diabetes," The Lancet 339:458-59, 1992.
Baekkeskov et al., "Antibodies to a 64,000 Mr Human Islet Cell Antigen Precede the Clinical Onset of Insulin- dependent Diabetes," J. Clin. Invest. 79:926-934, 1987.
Baekkeskov et al., "Autoantibodies in newly diagnosed diabetic children immunoprecipitate human pancreatic islet cell proteins," Nature 298:167-169, 1982.
Baekkeskov et al., "Identification of the 64K autoantigen in insulin-dependent diabetes as the GABA- synthesizing enzyme glutamic acid decarboxylase," Nature 347:151-156, 1990.
Bingley et al., "Perspectives in Diabetes, Can We Really Predict IDDM?" Diabetes 42:213-20, 1993.
Bingley et al., "Prediction of IDDM in the General Population, Strategies Based on Combinations of Autoanti- body Markers," Diabetes 46:1701-1710, 1997.
Bonifacio et al., "IA-2 (Islet Cell Antigen 512) Is the Primary Target of Humoral Autoimmunity Against Type I Diabetes-Associated Tyrosine Phosphatase Autoantigens," The Journal of Immunology 161:2648-2654, 1998.
Bonifacio et al., "Identification of Protein Tyrosine Phosphatase-Like IA2 (Islet Cell Antigen 512) as the Insulin-Dependent Diabetes-Related 37/40K . . . Antibodies," The Journal of Immunology 155:5419-5426, 1995.
Castano et al., "Characterization of Insulin Autoantibodies in Relatives of Patients with Type I Diabetes," Diabetes 42:1202-209, 1993.
Castano et al., "Type-I Diabetes: A Chronic Autoimmune Disease of Human, Mouse, and Rat," Annu. Rev. Immunol. 8:647-79, 1990.
Chicz et al., "Analysis of MHC-presented peptides: applications in autoimmunity and vaccine development," Immunology Today 15(4):155-160, 1994.
Chicz et al., "HLA-DP2—Self Peptide Sequences and Binding Properties," J. of Immunology 159:4935-4942,1997.
Chicz et al., "Predominant naturally processed peptides bound to HLA-DR1 are derived from MHC-related molecules and are heterogeneous in size," Nature 358:764-768, 1992.
Chicz et al., "Specificity and Promiscuity among Naturally Processed Peptides Bound to HLA-DR Alleles," J. Exp. Med. 178:27-47, 1993.
Chilson et al., "Mitogenic lectins bind to the antigen receptor on human lymphocytes," Eur. J. Immunol. 19:389-396, 1989.
Christie et al., "Antibodies to Islet 37k Antigen, But Not to Glutamate-Decarboxylase, Discriminate Rapid Progression to IDDM in Endocrine Autoimmunity," Diabetes 43:1254-1259, 1994.
Christie et al., "Distinct Antibody Specificities to a 64-kD Islet Cell Antigen in Type 1 Diabetes as Revealed by Trypsin Treatment," J. Exp. Med. 172:789-794, 1990.
Combadiere et al., "Selective Induction of Apoptosis in Mature T Lymphocytes by Variant T Cell Receptor Ligands," The J. of Experimental Medicine 187(3):349-355, 1998.

(Continued)

*Primary Examiner*—David A. Saunders
*Assistant Examiner*—F. Pierre VanderVegt
(74) *Attorney, Agent, or Firm*—Fish & Richardson P.C.

(57) ABSTRACT

The invention provides methods for identifying peptide epitopes that activate CD4+ T cells involved in the pathogenesis of diseases, e.g., autoimmune diseases, susceptibility to which is determined by expression of particular class II MHC genes. The invention includes peptides derived from the IA-2 polypeptide by such a method, altered peptide ligands, and methods of therapy involving the use of altered peptide ligands.

7 Claims, 3 Drawing Sheets

OTHER PUBLICATIONS

Congia et al., "T cell epitopes of insulin defined in HLA-DR4 transgenic mice are derived from preproinsulin and proinsulin," Proc. Natl. Acad. Sci. USA 95:3833-3838, 1998.

Das et al., "Autopathogenic T Helper Cell Type 1 (Th1) and Protective Th2 Clones Differ in Their Recognition of the Autoantigenic Peptide of Myelin Proteolipid Protein," J. Exp. Med. 186(6):867-876, 1997.

Davies et al., "A genome-wide search for human type 1 diabetes susceptibility genes," Nature 371:130-36,1994.

De Aizpurua et al., "Glutamic acid decarboxylase autoantibodies in preclinical insulin-dependent diabetes," Proc. Natl. Acad. Sci. USA 89:9841-9845, 1992.

Endi et al., "Identification of Naturally Processed T Cell Epitopes from Glutamic Acid Decarboxylase Presented . . . Patients," J. Clin. Invest. 99(10):2405-2415, 1997.

Germain, "MHC-Dependent Antigen Processing and Peptide Presentation: Providing Ligands for T Lymphocyte Activation," Cell 76(2):287-99, 1994.

Giorda et al., "Glutamic acid decarboxylase expression in islets and brain," The Lancet 338:1469-70, 1991.

Gorga et al., "Purification and Characterization of Class II Histocompatibility Antigens from a Homozygous Human B Cell Line," The J. of Biological Chemistry 262(33):16087-16094, 1987.

Haselden et al., "Immunoglobulin E-independent Major Histocompatibility . . . ," J. Exp. Med. 189(12):1855-1894, Jun. 21, 1999.

Honeyman et al., "Neural network-based prediction of candidate T-cell epitopes," Nature Biotechnology 16:966-969, 1998.

Honeyman et al., "Strategies for Identifying and Predicting Islet Autoantigen T-cell Epitopes in Insulin-dependent Diabetes Mellitus," Annals of Medicine 29:401-404, 1997.

Honeyman et al., "T-Cell Epitopes in Type 1 Diabetes Autoantigen Tyrosine Phosphatase IA-2: Potential for Mimicry with Rotavirus and Other Environmental Agents," Molecular Medicine 4:231-239, 1998.

Janeway et al., Immunobiology 4th Edition (1994) Garland Press USA, p. 568.

Kawasaki et al., "Evaluation of Islet Cell Antigen (ICA) 512/IA-2 Autoantibody Radioassays Using Overlapping ICA512/IA-2 Constructs," JCE & M 82(2):375-380, 1997.

Khalil et al., "Dose Effect of Cis- and Trans-Encoded HLA-DQαβ Heterodimers in IDDM Susceptibility," Diabetes 41:378-384, 1992.

Krebs et al., "Substituting Nonpeptidic Spacers for the T Cell Receptor-binding Part of Class I Major Histocompatibility Complex-binding Peptides," The J. of Biological Chemistry 273(30):19072-19079, 1998.

Kuglin et al., "Antibodies to Proinsulin and Insulin as Predictive Markers of Type 1 Diabetes," Diabetic Medicine 7:310-314, 1990.

Kwok et al., "HLA-DQB1 Codon 57 Is Critical for Peptide Binding and Recognition," J. Exp. Med 183:1253-1258, 1996.

Lohmann et al., "Immunodominant epitopes of glutamic acid decarboxylase 65 and 67 in insulin-dependent diabetes mellitus," The Lancet 343:1607-1608, 1994.

Lohmann et al., "T cell reactivity to DR*0401- and DQ*0302-binding peptides of the putative autoantigen IA-2 in type 1 diabetes," Exp. Clin. Endocrinl. Diabetes 107:166-171, 1999.

Marsh, "HLA class II region sequences," Tissue Antigens 51:467-507, 1998.

Nepom et al., "Perspectives in Diabetes: Molecular Basis for HLA-DQ Associations with IDDM," Diabetes 47: 1177-1184, 1998.

Nepom, "Class II Antigens and Disease Susceptibility," Annu. Rev. Med. 46:17-25, 1995.

Nicholson et al., "A T cell receptor antagonist peptide induces T cells that mediate bystander suppression and prevent autoimmune encephalomyelitis . . . antigens," Proc. Natl. Acad. Sci. USA 94:9279-9284, 1997.

Nicholson et al., "An Altered Peptide Ligand Mediates Immune Deviation and Prevents Autoimmune Encephalomyelitis," Immunity 3:397-405, 1995.

Nicholson et al., "Heteroclitic proliferative responses and changes in cytokine profile induced by altered peptides: Implications for autoimmunity," Proc. Natl. Acad. Sci. USA 95:264-269, 1998.

Nicholson et al., "Manipulation of the Th1/Th2 balance in autoimmune disease," Current Opinion in Immunology 8:837-842, 1996.

Nijman et al., "Characterization of cytotoxic T Lymphocyte Epitopes of a Self-Protein, p53, and a Non-Self-Protein, Influenza Matrix: Relationship Between Major Histocompatibility Complex Peptide Binding Affinity and Immune Responsiveness to Peptides," Journal of Immunotherapy 14:121-126, 1993.

Patel et al., "Identification of immunodominant T cell epitopes of human glutamic acid decarboxylase 65 by using HLA-DR . . . mice," Proc. Natl. Acad. Sci. USA 94:8082-8087, 1997.

Payton et al., "Relationship of the 37,000- and 40,000-Mr Tryptic Fragments of Islet Antigens in Insulin-dependent Diabetes . . . (ICA512)," J. Clin. Invest. 96:1506-1511, 1995.

Peakman et al., "Naturally processed and presented epitopes of the islet cell autoantigen IA-2 eluted from HLA-DR4," J. Clin. Invest. 104:1449-1457, 1999.

Petersen et al., "Detection of GAD65 Antibodies in Diabetes and Other Autoimmune Diseases Using a Simple Radioligand Assay," Diabetes 43:459-467, 1994.

Rabin et al., "Islet Cell Antigen 512 Is a Diabetes-Specific Islet Autoantigen Related to Protein Tyrosine Phosphatases," J. of Immunology 152:3183-3188, 1994.

Roep, "Perspectives in Diabetes: T-Cell Responses to Autoantigens in IDDM—The Search for the Holy Grail," Diabetes 45:1147-1155, 1996.

Seissler et al., "Prevalence of Autoantibodies to the 65- and 67-kD Isoforms of Glutamate Decarboxylase in Insulin-dependent Diabetes Mellitus," J. Clin. Invest. 92:1394-1399, 1993.

Steinman, "Escape from 'Horror Autotoxicus': Pathogenesis and Treatment of Autoimmune Disease," Cell 80:7-10, 1995.

Stevens et al., "Enhanced T cell proliferation and increased responder frequency following delivery of antigen to the antigen-presenting cell; B cell . . . cells," J. of Immunological Methods 215:59-70, 1998.

Tao et al., "Induction of IL-4-Producing CD4+ T Cells by Antigenic Peptides Altered for TCR Binding," The J. of Immunology 158:4237-4244, 1997.

Urban et al., "The Discovery and Use of HLA-Associated Epitopes as Drugs," Critical Reviews in Immunology 17:387-397, 1997.

Vignali et al., "Minute quantities of a single immunodominant foreign epitope are presented as large nested sets . . . molecules," Eur. J. Immunol. 23:1602-1607, 1993.

Vincent et al., "Characterization of specific T cells in myasthenia gravis," Immunology Today 15(1):41-42, 1994.

Wicker et al., "Naturally Processed T Cell Epitopes from Human Gutamic Acid Decarboxylase Identified Using Mice Transgenic . . . DRB1*0401," J. Clin. Invest. 98(11):2597-2603, 1996.

SEQUENCE LISTING

<160> NUMBER OF SEQ ID NOS: 55

<210> SEQ ID NO 1
<211> LENGTH: 15
<212> TYPE: PRT
<213> ORGANISM: Homo sapiens

<400> SEQUENCE: 1

Val Ser Ser Gln Phe Ser Asp Ala Ala Gln Ala Ser Pro Ser Ser
 1               5                  10                  15

<210> SEQ ID NO 2

-continued

```
<211> LENGTH: 15
<212> TYPE: PRT
<213> ORGANISM: Homo sapiens

<400> SEQUENCE: 2

Ser Val Ser Ser Gln Phe Ser Asp Ala Ala Gln Ala Ser Pro Ser
 1               5                  10                  15

<210> SEQ ID NO 3
<211> LENGTH: 15
<212> TYPE: PRT
<213> ORGANISM: Homo sapiens

<400> SEQUENCE: 3

Ser Ser Val Ser Ser Gln Phe Ser Asp Ala Ala Gln Ala Ser Pro
 1               5                  10                  15

<210> SEQ ID NO 4
<211> LENGTH: 19
<212> TYPE: PRT
<213> ORGANISM: Homo sapiens

<400> SEQUENCE: 4

Ser Val Ser Ser Gln Phe Ser Asp Ala Ala Gln Ala Ser Pro Ser Ser
 1               5                  10                  15

His Ser Ser

<210> SEQ ID NO 5
<211> LENGTH: 24
<212> TYPE: PRT
<213> ORGANISM: Homo sapiens

<400> SEQUENCE: 5

Ser Arg Val Ser Ser Val Ser Ser Gln Phe Ser Asp Ala Ala Gln Ala
 1               5                  10                  15

Ser Pro Ser Ser His Ser Ser Thr
                20

<210> SEQ ID NO 6
<211> LENGTH: 24
<212> TYPE: PRT
<213> ORGANISM: Homo sapiens

<400> SEQUENCE: 6

Ser Val Ser Ser Gln Phe Ser Asp Ala Ala Gln Ala Ser Pro Ser Ser
 1               5                  10                  15

His Ser Ser Thr Pro Ser Trp Cys
                20

<210> SEQ ID NO 7
<211> LENGTH: 24
<212> TYPE: PRT
<213> ORGANISM: Homo sapiens

<400> SEQUENCE: 7

Val Ser Ser Gln Phe Ser Asp Ala Ala Gln Ala Ser Pro Ser Ser His
 1               5                  10                  15

Ser Ser Thr Pro Ser Trp Cys Glu
                20

<210> SEQ ID NO 8
<211> LENGTH: 21
<212> TYPE: PRT
```

-continued

<213> ORGANISM: Homo sapiens

<400> SEQUENCE: 8

Val Ser Ser Val Ser Ser Gln Phe Ser Asp Ala Ala Gln Ala Ser Pro
1               5                   10                  15

Ser Ser His Ser Ser
            20

<210> SEQ ID NO 9
<211> LENGTH: 12
<212> TYPE: PRT
<213> ORGANISM: Homo sapiens

<400> SEQUENCE: 9

Thr Gln Glu Thr Arg Thr Leu Thr Gln Phe His Phe
1               5                   10

<210> SEQ ID NO 10
<211> LENGTH: 13
<212> TYPE: PRT
<213> ORGANISM: Homo sapiens

<400> SEQUENCE: 10

Tyr Leu Lys Asn Val Gln Thr Gln Glu Thr Arg Thr Leu
1               5                   10

<210> SEQ ID NO 11
<211> LENGTH: 14
<212> TYPE: PRT
<213> ORGANISM: Homo sapiens

<400> SEQUENCE: 11

Val Gln Thr Gln Glu Thr Arg Thr Leu Thr Gln Phe His Phe
1               5                   10

<210> SEQ ID NO 12
<211> LENGTH: 15
<212> TYPE: PRT
<213> ORGANISM: Homo sapiens

<400> SEQUENCE: 12

Leu Lys Asn Val Gln Thr Gln Glu Thr Arg Thr Leu Thr Gln Phe
1               5                   10                  15

<210> SEQ ID NO 13
<211> LENGTH: 15
<212> TYPE: PRT
<213> ORGANISM: Homo sapiens

<400> SEQUENCE: 13

Tyr Leu Lys Asn Val Gln Thr Gln Glu Thr Arg Thr Leu Thr Gln
1               5                   10                  15

<210> SEQ ID NO 14
<211> LENGTH: 15
<212> TYPE: PRT
<213> ORGANISM: Homo sapiens

<400> SEQUENCE: 14

Lys Asn Val Gln Thr Gln Glu Thr Arg Thr Leu Thr Gln Phe His
1               5                   10                  15

<210> SEQ ID NO 15
<211> LENGTH: 19

<212> TYPE: PRT
<213> ORGANISM: Homo sapiens

<400> SEQUENCE: 15

Ser Phe Tyr Leu Lys Asn Val Gln Thr Gln Glu Thr Arg Thr Leu Thr
1               5                   10                  15

Gln Phe His

<210> SEQ ID NO 16
<211> LENGTH: 19
<212> TYPE: PRT
<213> ORGANISM: Homo sapiens

<400> SEQUENCE: 16

Phe Tyr Leu Lys Asn Val Gln Thr Gln Glu Thr Arg Thr Leu Thr Gln
1               5                   10                  15

Phe His Phe

<210> SEQ ID NO 17
<211> LENGTH: 13
<212> TYPE: PRT
<213> ORGANISM: Homo sapiens

<400> SEQUENCE: 17

Ala Tyr Gln Ala Glu Pro Asn Thr Cys Ala Thr Ala Gln
1               5                   10

<210> SEQ ID NO 18
<211> LENGTH: 16
<212> TYPE: PRT
<213> ORGANISM: Homo sapiens

<400> SEQUENCE: 18

Leu Cys Ala Tyr Gln Ala Glu Pro Asn Thr Cys Ala Thr Ala Gln Gly
1               5                   10                  15

<210> SEQ ID NO 19
<211> LENGTH: 17
<212> TYPE: PRT
<213> ORGANISM: Homo sapiens

<400> SEQUENCE: 19

Leu Ala Lys Glu Trp Gln Ala Leu Cys Ala Tyr Gln Ala Glu Pro Asn
1               5                   10                  15

Thr

<210> SEQ ID NO 20
<211> LENGTH: 19
<212> TYPE: PRT
<213> ORGANISM: Homo sapiens

<400> SEQUENCE: 20

Ala Tyr Gln Ala Glu Pro Asn Thr Cys Ala Thr Ala Gln Gly Glu Gly
1               5                   10                  15

Asn Ile Lys

<210> SEQ ID NO 21
<211> LENGTH: 18
<212> TYPE: PRT
<213> ORGANISM: Homo sapiens

<400> SEQUENCE: 21

-continued

Trp Gln Ala Leu Cys Ala Tyr Gln Ala Glu Pro Asn Thr Cys Ala Thr
1               5                   10                  15

Ala Gln

<210> SEQ ID NO 22
<211> LENGTH: 24
<212> TYPE: PRT
<213> ORGANISM: Homo sapiens

<400> SEQUENCE: 22

Leu Ala Lys Glu Trp Gln Ala Leu Cys Ala Tyr Gln Ala Glu Pro Asn
1               5                   10                  15

Thr Cys Ala Thr Ala Gln Gly Glu
            20

<210> SEQ ID NO 23
<211> LENGTH: 14
<212> TYPE: PRT
<213> ORGANISM: Homo sapiens

<400> SEQUENCE: 23

Gly Cys Thr Val Ile Val Met Leu Thr Pro Leu Val Glu Asp
1               5                   10

<210> SEQ ID NO 24
<211> LENGTH: 14
<212> TYPE: PRT
<213> ORGANISM: Homo sapiens

<400> SEQUENCE: 24

Cys Thr Val Ile Val Met Leu Thr Pro Leu Val Glu Asp Gly
1               5                   10

<210> SEQ ID NO 25
<211> LENGTH: 17
<212> TYPE: PRT
<213> ORGANISM: Homo sapiens

<400> SEQUENCE: 25

Glu Ser Gly Cys Thr Val Ile Val Met Leu Thr Pro Leu Val Glu Asp
1               5                   10                  15

Gly

<210> SEQ ID NO 26
<211> LENGTH: 16
<212> TYPE: PRT
<213> ORGANISM: Homo sapiens

<400> SEQUENCE: 26

Met Val Trp Glu Ser Gly Cys Thr Val Ile Val Met Leu Thr Pro Leu
1               5                   10                  15

<210> SEQ ID NO 27
<211> LENGTH: 18
<212> TYPE: PRT
<213> ORGANISM: Homo sapiens

<400> SEQUENCE: 27

Ser Gly Cys Thr Val Ile Val Met Leu Thr Pro Leu Val Glu Asp Gly
1               5                   10                  15

Val Lys

```
<210> SEQ ID NO 28
<211> LENGTH: 18
<212> TYPE: PRT
<213> ORGANISM: Homo sapiens

<400> SEQUENCE: 28

Glu Ser Gly Cys Thr Val Ile Val Met Leu Thr Pro Leu Val Glu Asp
 1               5                  10                  15

Gly Val

<210> SEQ ID NO 29
<211> LENGTH: 16
<212> TYPE: PRT
<213> ORGANISM: Homo sapiens

<400> SEQUENCE: 29

Trp Gln Met Val Trp Glu Ser Gly Cys Thr Val Ile Val Met Leu Thr
 1               5                  10                  15

<210> SEQ ID NO 30
<211> LENGTH: 18
<212> TYPE: PRT
<213> ORGANISM: Homo sapiens

<400> SEQUENCE: 30

Asp Phe Trp Gln Met Val Trp Glu Ser Gly Cys Thr Val Ile Val Met
 1               5                  10                  15

Leu Thr

<210> SEQ ID NO 31
<211> LENGTH: 20
<212> TYPE: PRT
<213> ORGANISM: Homo sapiens

<400> SEQUENCE: 31

Phe Trp Gln Met Val Trp Glu Ser Gly Cys Thr Val Ile Val Met Leu
 1               5                  10                  15

Thr Pro Leu Val
         20

<210> SEQ ID NO 32
<211> LENGTH: 21
<212> TYPE: PRT
<213> ORGANISM: Homo sapiens

<400> SEQUENCE: 32

Met Val Trp Glu Ser Gly Cys Thr Val Ile Val Met Leu Thr Pro Leu
 1               5                  10                  15

Val Glu Asp Gly Val
             20

<210> SEQ ID NO 33
<211> LENGTH: 13
<212> TYPE: PRT
<213> ORGANISM: Homo sapiens

<400> SEQUENCE: 33

Asp Gln Phe Glu Phe Ala Leu Thr Ala Val Ala Glu Glu
 1               5                  10

<210> SEQ ID NO 34
<211> LENGTH: 17
<212> TYPE: PRT
```

<213> ORGANISM: Homo sapiens

<400> SEQUENCE: 34

Asp Gln Phe Glu Phe Ala Leu Thr Ala Val Ala Glu Glu Val Asn Ala
 1               5                  10                  15
Ile

<210> SEQ ID NO 35
<211> LENGTH: 18
<212> TYPE: PRT
<213> ORGANISM: Homo sapiens

<400> SEQUENCE: 35

Phe Glu Phe Ala Leu Thr Ala Val Ala Glu Glu Val Asn Ala Ile Leu
 1               5                  10                  15
Lys Ala

<210> SEQ ID NO 36
<211> LENGTH: 18
<212> TYPE: PRT
<213> ORGANISM: Homo sapiens

<400> SEQUENCE: 36

Ser Lys Asp Gln Phe Glu Phe Ala Leu Thr Ala Val Ala Glu Glu Val
 1               5                  10                  15
Asn Ala

<210> SEQ ID NO 37
<211> LENGTH: 21
<212> TYPE: PRT
<213> ORGANISM: Homo sapiens

<400> SEQUENCE: 37

Ser Lys Asp Gln Phe Glu Phe Ala Leu Thr Ala Val Ala Glu Glu Val
 1               5                  10                  15
Asn Ala Ile Leu Lys
             20

<210> SEQ ID NO 38
<211> LENGTH: 12
<212> TYPE: PRT
<213> ORGANISM: Homo sapiens

<400> SEQUENCE: 38

Lys Val Glu Ser Ser Pro Ser Arg Ser Asp Tyr Ile
 1               5                  10

<210> SEQ ID NO 39
<211> LENGTH: 12
<212> TYPE: PRT
<213> ORGANISM: Homo sapiens

<400> SEQUENCE: 39

Leu Lys Val Glu Ser Ser Pro Ser Arg Ser Asp Tyr
 1               5                  10

<210> SEQ ID NO 40
<211> LENGTH: 17
<212> TYPE: PRT
<213> ORGANISM: Homo sapiens

<400> SEQUENCE: 40

-continued

Lys Leu Lys Val Glu Ser Ser Pro Ser Arg Ser Asp Tyr Ile Asn Ala
1               5                   10                  15
Ser

<210> SEQ ID NO 41
<211> LENGTH: 22
<212> TYPE: PRT
<213> ORGANISM: Homo sapiens

<400> SEQUENCE: 41

Lys Val Glu Ser Ser Pro Ser Arg Ser Asp Tyr Ile Asn Ala Ser Pro
1               5                   10                  15
Ile Ile Glu His Asp Pro
            20

<210> SEQ ID NO 42
<211> LENGTH: 19
<212> TYPE: PRT
<213> ORGANISM: Homo sapiens

<400> SEQUENCE: 42

Leu Lys Val Glu Ser Ser Pro Ser Arg Ser Asp Tyr Ile Asn Ala Ser
1               5                   10                  15
Pro Ile Ile

<210> SEQ ID NO 43
<211> LENGTH: 25
<212> TYPE: PRT
<213> ORGANISM: Homo sapiens

<400> SEQUENCE: 43

Met Ala Ile Ser Gly Val Pro Val Leu Gly Phe Phe Ile Ile Ala Val
1               5                   10                  15
Leu Met Ser Ala Gln Glu Ser Trp Ala
            20                  25

<210> SEQ ID NO 44
<211> LENGTH: 5
<212> TYPE: PRT
<213> ORGANISM: Bovine

<400> SEQUENCE: 44

Lys Phe Glu Arg Gln
1               5

<210> SEQ ID NO 45
<211> LENGTH: 15
<212> TYPE: PRT
<213> ORGANISM: Homo sapiens

<400> SEQUENCE: 45

Met Asp Asp Gln Arg Asp Leu Ile Ser Asn Asn Glu Gln Leu Pro
1               5                   10                  15

<210> SEQ ID NO 46
<211> LENGTH: 4
<212> TYPE: PRT
<213> ORGANISM: Rattus rattus

<400> SEQUENCE: 46

Lys Asp Glu Leu
1

-continued

<210> SEQ ID NO 47
<211> LENGTH: 13
<212> TYPE: PRT
<213> ORGANISM: Homo sapiens

<400> SEQUENCE: 47

Val Ser Ser Gln Phe Ser Asp Ala Ala Gln Ala Ser Pro
 1               5                  10

<210> SEQ ID NO 48
<211> LENGTH: 7
<212> TYPE: PRT
<213> ORGANISM: Homo sapiens

<400> SEQUENCE: 48

Thr Gln Glu Thr Arg Thr Leu
 1               5

<210> SEQ ID NO 49
<211> LENGTH: 8
<212> TYPE: PRT
<213> ORGANISM: Homo sapiens

<400> SEQUENCE: 49

Ala Tyr Gln Ala Glu Pro Asn Thr
 1               5

<210> SEQ ID NO 50
<211> LENGTH: 11
<212> TYPE: PRT
<213> ORGANISM: Homo sapiens

<400> SEQUENCE: 50

Phe Glu Phe Ala Leu Thr Ala Val Ala Glu Glu
 1               5                  10

<210> SEQ ID NO 51
<211> LENGTH: 8
<212> TYPE: PRT
<213> ORGANISM: Homo sapiens

<400> SEQUENCE: 51

Cys Thr Val Ile Val Met Leu Thr
 1               5

<210> SEQ ID NO 52
<211> LENGTH: 11
<212> TYPE: PRT
<213> ORGANISM: Homo sapiens

<400> SEQUENCE: 52

Lys Val Glu Ser Ser Pro Ser Arg Ser Asp Tyr
 1               5                  10

<210> SEQ ID NO 53
<211> LENGTH: 5
<212> TYPE: PRT
<213> ORGANISM: Homo sapiens

<400> SEQUENCE: 53

Gln Lys Arg Ala Ala
 1               5

<210> SEQ ID NO 54

```
<211> LENGTH: 5
<212> TYPE: PRT
<213> ORGANISM: Homo sapiens

<400> SEQUENCE: 54

Gln Arg Arg Ala Ala
 1               5

<210> SEQ ID NO 55
<211> LENGTH: 5
<212> TYPE: PRT
<213> ORGANISM: Homo sapiens

<400> SEQUENCE: 55

Arg Arg Arg Ala Ala
 1               5
```

PEPTIDE EPITOPES RECOGNIZED BY DISEASE PROMOTING CD4+ T LYMPHOCYTES

CROSS-REFERENCE TO RELATED APPLICATIONS

This application is a divisional of U.S. application Ser. No. 10/378,479, filed on Mar. 3, 2003, which is a divisional of U.S. application Ser. No. 09/552,802, filed on Apr. 20, 2000, issued on May 13, 2003 as U.S. Pat. No. 6,562,943, which claims priority to U.S. Provisional Application Ser. No. 60/130,355, filed on Apr. 21, 1999. The disclosures of the prior applications are incorporated herein by reference in their entirety.

BACKGROUND OF THE INVENTION

The invention is in the field of diseases with an immunological aetiology, particularly diseases involving CD4+ T lymphocytes.

After internalization and proteolytic processing of intact protein antigens by antigen presenting cells (APCs) class II Major Histocompatibility Complex (MHC) molecules on the APCs bind short antigenic peptides (epitopes) derived from the antigens, presenting the bound peptides to CD4+ T lymphocytes [Germain, R. N. (1994), Cell 76:287-299]. Class II MHC genes and the molecules they encode are highly variable between individuals, and differences between the class II MHC molecules have profound effects on which peptides are selected for presentation as T cell epitopes. The different forms (alleles) of class II MHC molecules expressed by an individual have a major effect on the individual's susceptibility to a range of CD4+ T cell-mediated diseases, most notably autoimmune disease such as insulin dependent diabetes mellitus (IDDM) [Davies et al. (1994), Nature 371:130-136]. It is important that the antigenic epitopes of antigens recognized by the CD4+ T cells mediating these diseases be defined in order to develop effective therapeutic and/or prophylactic products and protocols.

U.S. Pat. No. 5,827,516 is incorporated herein by reference in its entirety.

SUMMARY OF THE INVENTION

The invention features methods for identifying peptide epitopes that activate CD4+ T lymphocyte responses involved in the initiation, promotion, or exacerbation of certain diseases, especially those in which susceptibility is determined by expression of defined class II MHC molecules. The methods are based on the discovery that artificially binding a polypeptide molecule to the cell membrane of an APC facilitates transport of the molecule to the antigen processing organelles of the APC. The invention includes peptides derived by such a method from the diabetes autoantigen, IA-2. Altered peptide ligands (APL), which are variant peptides in which 1 to 6 amino acid residues are different from the corresponding residues of the wild-type peptide, but which still bind to the same class II MHC molecules as the wild-type peptides, are also encompassed by the invention, as are methods of therapy and prophylaxis involving the use of APL. APL have the ability to elicit different patterns of cytokine production in CD4 T cells than do their parent wild-type peptides. Thus, for example, while a wild-type peptide may induce production of Th1 cytokines, an APL derived from it may elicit Th2 cytokines. Alternatively, the wild-type peptide may stimulate the production of Th2 cytokines and a corresponding APL elicits production of Th1 cytokines.

Specifically, the invention features a method of identifying a class II MHC-binding fragment of a polypeptide which involves the steps of: (a) providing a ligand conjugated with a first biotin moiety; (b) providing the polypeptide conjugated with a second biotin moiety; (c) providing a mammalian antigen-presenting cell (APC) expressing a class II MHC molecule and a cell surface receptor which binds the ligand; (d) contacting the APC with the biotin-conjugated ligand of (a), the biotin-conjugated polypeptide of (b), and avidin, to form a complex which binds to the cell surface receptor; (e) maintaining the APC under conditions which allow internalization of the complex by the APC; (f) isolating from the APC a class II MHC molecule bound to a peptide; and (g) eluting the peptide from the class II MHC molecule, the peptide being a class II MHC-binding fragment of the polypeptide. The method can further involve the step of identifying the amino acid sequence of the peptide. The method can be applied to the identification of a peptide, the presentation of which by a class II MHC molecule on an APC of a mammal is associated with either pathology of a mammalian disease or with protection from a mammalian disease. Appropriate diseases include autoimmune diseases (e.g., insulin-dependent diabetes mellitus (IDDM), multiple sclerosis, rheumatoid arthritis, myasthenia gravis, systemic lupus erythematosus, autoimmune premature ovarian failure, Graves' thyroiditis, Hashimoto's thyroiditis, primary hypothyroidism, coeliac disease, primary biliary cirrhosis, autoimmune hepatitis, Addison's disease, vitiligo, systemic sclerosis, or anti-glomerular basement membrane disease), infectious diseases (e.g., a bacterial disease such as leprosy, a viral disease, or a parasitic disease), or cancer. Where the autoimmune disease is IDDM, the polypeptide can be preproinsulin, proinsulin, insulin, glutamic acid decarboxylase (GAD65), IA-2 tyrosine phosphatase (IA-2), or phogrin (IA-2β). The APC used in the method can be a dendritic cell, a macrophage, a monocyte, or a B lymphocyte. The ligand used can be a lectin molecule (e.g., pokeweed mitogen from *Phytolacca americana*) that binds to a cell surface receptor (e.g., a surface immunoglobulin molecule) on an APC. The cell surface receptor targeted by the method of the invention can be a cell surface molecule (e.g., an immunoglobulin molecule) that can be internalized by the APC and the ligand can be an antibody molecule which binds to the cell surface molecule. The mammal from which the APC is derived can be a human and the class II MHC molecule can be a DR molecule with a β-chain encoded by a DRB1*0401, DRB1*0405, or DRB1*0101 gene. Alternatively, the class II MHC molecule can be a DQ molecule with an a-chain encoded by a DQA1*0501 or DQA1*0301 gene and a β-chain encoded by a DQB1*0302, DQB1*0201, or DQB1*0501 gene.

The described method can include the additional steps of: (h) providing CD4 lymphocytes from an individual suspected of being susceptible to a condition associated with presentation of the peptide by the class II MHC molecule, the individual's APCs bearing the class II MHC molecule; (i) providing a population of APCs which bear the class II MHC molecule with the peptide bound thereto; (j) contacting the population of APCs of (i) with the CD4 lymphocytes of (h); and (k) determining whether the CD4 lymphocytes recognize the class II MHC-bound peptide. The presentation of the peptide can result in either a pathological response of CD4+ T lymphocytes or a protective response of CD4+ T lymphocytes.

The invention also includes an isolated peptide less than 26 amino acid residues in length and containing a sequence VSSQFSDAAQASP (SEQ ID NO:47), e.g., VSSQFS-DAAQASPSS (SEQ ID NO:1); SVSSQFSDAAQASPS (SEQ ID NO:2); SSVSSQFSDAAQASP (SEQ ID NO:3); SVSSQFSDAAQASPSSHSS (SEQ ID NO:4); SRVSS-VSSQFSDAAQASPSSHSST (SEQ ID NO:5); SVSSQFS-DAAQASPSSHSSTPSWC (SEQ ID NO:6); VSSQFS-DAAQASPSSHSSTPSWCE (SEQ ID NO:7); or VSSVSSQFSDAAQASPSSHSS (SEQ ID NO:8). The isolated peptide can also be less than 26 amino acid residues in length and contain a sequence TQETRTL (SEQ ID NO:48), e.g., TQETRTLTQFHF (SEQ ID NO:9); YLKN-VQTQETRTL (SEQ ID NO:10); VQTQETRTLTQFHF (SEQ ID NO:11); LKNVQTQETRTLTQF (SEQ ID NO:12); YLKNVQTQETRTLTQ (SEQ ID NO:13); KNVQTQETRTLTQFH (SEQ ID NO:14); SFYLKN-VQTQETRTLTQFH (SEQ ID NO:15); or FYLKN-VQTQETRTLTQFHF (SEQ ID NO:16). Other embodiments include an isolated peptide less than 26 amino acid residues in length and containing a sequence AYQAEPNT (SEQ ID NO:49), a sequence CTVIVMLT (SEQ ID NO:51) FEFAL-TAVAEE (SEQ ID NO:50), or a sequence KVESSPSRSDY (SEQ ID NO:52). Examples of such peptides are AYQAEP-NTCATAQ (SEQ ID NO:17); LCAYQAEPNTCATAQG (SEQ ID NO:18); LAKEWQALCAYQAEPNT (SEQ ID NO:19); AYQAEPNTCATAQGEGNIK (SEQ ID NO:20); WQALCAYQAEPNTCATAQ (SEQ ID NO:21); LAKEWQALCAYQAEPNTCATAQGE (SEQ ID NO:22); DQFEFALTAVAEE (SEQ ID NO:33); DQFEFALTA-VAEEVNAI (SEQ ID NO:34); FEFALTAVAEEVNAILKA (SEQ ID NO:35); SKDQFEFALTAVAEEVNA (SEQ ID NO:36); SKDQFEFALTAVAEEVNAILK (SEQ ID NO:37); GCTVIVMLTPLVED (SEQ ID NO:23); CTVIVMLTPL-VEDG (SEQ ID NO:24); ESGCTVIVMLTPLVEDG (SEQ ID NO:25); MVWESGCTVIVMLTPL (SEQ ID NO:26); SGCTVIVMLTPLVEDGVK (SEQ ID NO:27); ESGCTVIVMLTPLVEDGV (SEQ ID NO:28); WQM-VWESGCTVIVMLT (SEQ ID NO:29); DFWQMVWES-GCTVIVMLT (SEQ ID NO:30); FWQMVWESGCTVIVM-LTPLV (SEQ ID NO:31); MVWESGCTVIVMLTPLVEDGV (SEQ ID NO:32); KVESSPSRSDYI (SEQ ID NO:38); LKVESSPSRSDY (SEQ ID NO:39); KLKVESSPSRSDYINAS (SEQ ID NO:40); KVESSPSRSDYINASPIIEHDP (SEQ ID NO:41); and LKVESSPSRSDYINASPII (SEQ ID NO:42).

The invention also features a method of protecting a subject from IDDM or the pathogenic symptoms of IDDM. It is understood that protecting includes alleviating (or decreasing) as well as eliminating the pathogenic symptoms in a subject. The method includes administering any of the above peptides of the invention to the subject by any of the routes disclosed herein.

Also encompassed by the invention are altered peptide ligands, the amino acid sequence of which is identical, except for 1-6 amino acid substitutions, to a fragment of IA-2, the fragment being less than 26 amino acids residues in length and containing a sequence AYQAEPNT (SEQ ID NO:49); VSSQFSDAAQASP (SEQ ID NO:47); TQETRTL (SEQ ID NO:48); CTVIVMLT (SEQ ID NO:44); FEFALTAVAEE (SEQ ID NO:43); or KVESSPSRSDY (SEQ ID NO:52). In the altered peptide ligands, at least one but no more than 30% of the amino acid residues of the fragment are substituted with different amino acid residues. The sequences of the fragments from which the altered peptide ligands can be derived include: AYQAEPNTCATAQ (SEQ ID NO:17); LCAYQAEPNTCATAQG (SEQ ID NO:18); LAKEWQAL-CAYQAEPNT (SEQ ID NO:19); AYQAEPNTCATAQGEG-NIK (SEQ ID NO:20); WQALCAYQAEPNTCATAQ (SEQ ID NO:21); LAKEWQALCAYQAEPNTCATAQGE (SEQ ID NO:22); VSSQFSDAAQASPSS (SEQ ID NO:1); SVSSQFSDAAQASPS (SEQ ID NO:2); SSVSSQFS-DAAQASP (SEQ ID NO:3); SVSSQFSDAAQASPSSHSS (SEQ ID NO:4); SRVSSVSSQFSDAAQASPSSHSST (SEQ ID NO:5); SVSSQFSDAAQASPSSHSSTPSWC (SEQ ID NO:6); VSSQFSDAAQASPSSHSSTPSWCE (SEQ ID NO:7); VSSVSSQFSDAAQASPSSHSS (SEQ ID NO:8); TQETRTLTQFHF (SEQ ID NO:9); YLKNVQTQETRTL (SEQ ID NO:10); VQTQETRTLTQFHF (SEQ ID NO:11); LKNVQTQETRTLTQF (SEQ ID NO:12); YLKN-VQTQETRTLTQ (SEQ ID NO:13); KNVQTQETRTLTQFH (SEQ ID NO:14); SFYLKN-VQTQETRTLTQFH (SEQ ID NO:15); FYLKN-VQTQETRTLTQFHF (SEQ ID NO:16); GCTVIVMLT-PLVED (SEQ ID NO:23); CTVIVMLTPLVEDG (SEQ ID NO:24); ESGCTVIVMLTPLVEDG (SEQ ID NO:25); MVWESGCTVIVMLTPL (SEQ ID NO:26); SGCTVIVM-LTPLVEDGVK (SEQ ID NO:27); ESGCTVIVMLTPL-VEDGV (SEQ ID NO:28); WQMVWESGCTVIVMLT (SEQ ID NO:29); DFWQMVWESGCTVIVMLT (SEQ ID NO:30); FWQMVWESGCTVIVMLTPLV (SEQ ID NO:31); MVWESGCTVIVMLTPLVEDGV (SEQ ID NO:32); DQFEFALTAVAEE (SEQ ID NO:33); DQFEFAL-TAVAEEVNAI (SEQ ID NO:34); FEFALTAVAEEV-NAILKA (SEQ ID NO:35); SKDQFEFALTAVAEEVNA (SEQ ID NO:36); SKDQFEFALTAVAEEVNAILK (SEQ ID NO:37); KVESSPSRSDYI (SEQ ID NO:38); LKVESSPSRSDY (SEQ ID NO:39); KLKVESSPSRSDYI-NAS (SEQ ID NO:40); KVESSPSRSDYINASPIIEHDP (SEQ ID NO:41); and LKVESSPSRSDYINASPII (SEQ ID NO:42).

The invention also features a process of making an altered peptide ligand (APL) involving the following steps: (a) carrying out the above-described method of identifying a class II MHC-binding fragment of a polypeptide, including the step of identifying the amino acid sequence of the peptide eluted from the MHC class molecule, and (b) synthesizing an APL consisting of a sequence which is identical to that of the eluted peptide, except having amino acid substitutions at 1, 2, 3, 4, 5, or 6 positions in the peptide. The method can be performed using the polypeptides insulin, proinsulin, preproinsulin, IA-2, IA-2β, or GAD65.

Also within the invention is a method of reducing T cell autoreactivity in a mammal involving the following steps: (a) providing an APL having a sequence identical, except for amino acid substitutions at 1-6 positions, to that of a naturally-processed, diabetes-associated peptide fragment of insulin, proinsulin, preproinsulin, IA-2, IA-2β, or GAD65, the APL having the property of binding to a class II MHC molecule of the mammal; and (b) administering the APL, or a DNA encoding the APL, to the mammal.

The invention also provides a method of identifying a class II MHC-binding fragment of a polypeptide involving the following steps: (a) providing a ligand conjugated with a biotin moiety; (b) providing the polypeptide conjugated with an avidin moiety; (c) providing a mammalian APC expressing a class II MHC molecule and a cell surface receptor which binds the ligand; (d) contacting the APC with the biotin-conjugated ligand of (a) and the avidin-conjugated polypeptide of (b), to form a complex which binds to the cell surface receptor; (e) maintaining the APC under conditions which allow internalization of the complex by the APC; (f) isolating from the APC the class II MHC molecule bound to a peptide; and (g) eluting the peptide from the class II MHC molecule, the peptide being a class II MHC-binding fragment of the polypeptide. This method can include the following additional steps: (h) providing CD4 lymphocytes from an individual suspected of being susceptible to a condition associated with presentation of the peptide by the class II MHC molecule, the individual's APCs bearing the class II MHC molecule; (i) providing a population of APCs which bear the class II MHC molecule with the peptide bound thereto; (j) contacting the population of APCs of (i) with the CD4 lymphocytes of (h); and (k) determining whether the CD4 lymphocytes recognize the class II MHC-bound peptide, as an indication that the peptide is associated with the individual's condition. The presentation of the peptide can result in either a pathological response of CD4+ T lymphocytes or a protective response of CD4+ T lymphocytes. Naturally the method could be performed by conjugating the ligand with avidin and the polypeptide with biotin.

Another embodiment of the invention is a method of diagnosis comprising: (a) providing CD4 lymphocytes from an individual suspected of having or being susceptible to IDDM; (b) providing a population of APCs which bear on their surface a class II MHC molecule of an allele identical to one expressed by the individual, the population of APCs having been contacted with an IA-2 peptide and the class II MHC molecule of the APCs being bound to the IA-2 peptide; (c) contacting the population of APCs of (b) with the CD4 lymphocytes of (a); and (d) determining whether the CD4 lymphocytes recognize the class II MHC-bound peptide, as an indication that the individual has or is susceptible to IDDM. The IA-2 peptide used in the method can have the amino acid sequence: VSSQFSDAAQASPSS (SEQ ID NO:1); SVSSQFSDAAQASPS (SEQ ID NO:2); SSVSSQFS-DAAQASP (SEQ ID NO:3); SVSSQFSDAAQASPSSHSS (SEQ ID NO:4); SRVSSVSSQFSDAAQASPSSHSST (SEQ ID NO:5); SVSSQFSDAAQASPSSHSSTPSWC (SEQ ID NO:6); VSSQFSDAAQASPSSHSSTPSWCE (SEQ ID NO:7); VSSVSSQFSDAAQASPSSHSS (SEQ ID NO:8); TQETRTLTQFHF (SEQ ID NO:9); YLKNVQTQETRTL (SEQ ID NO:10); VQTQETRTLTQFHF (SEQ ID NO:11); LKNVQTQETRTLTQF (SEQ ID NO:12); YLKN-VQTQETRTLTQ (SEQ ID NO:13); KNVQTQETRTLTQFH (SEQ ID NO:14); SFYLKN-VQTQETRTLTQFH (SEQ ID NO:15); FYLKN-VQTQETRTLTQFHF (SEQ ID NO:16); AYQAEPNT-CATAQ (SEQ ID NO:17); LCAYQAEPNTCATAQG (SEQ ID NO:18); LAKEWQALCAYQAEPNT (SEQ ID NO:19); AYQAEPNTCATAQGEGNIK (SEQ ID NO:20); WQAL-CAYQAEPNTCATAQ (SEQ ID NO:21); LAKEWQAL-CAYQAEPNTCATAQGE (SEQ ID NO:22); GCTVIVMLT-PLVED (SEQ ID NO:23); CTVIVMLTPLVEDG (SEQ ID NO:24); ESGCTVIVMLTPLVEDG (SEQ ID NO:25); MVWESGCTVIVMLTPL (SEQ ID NO: 26); SGCTVIVM-LTPLVEDGVK (SEQ ID NO:27); ESGCTVIVMLTPL-VEDGV (SEQ ID NO:28); WQMVWESGCTVIVMLT (SEQ ID NO:29); DFWQMVWESGCTVIVMLT (SEQ ID NO:30); FWQMVWESGCTVIVMLTPLV (SEQ ID NO:31); MVWESGCTVIVMLTPLVEDGV (SEQ ID NO:32); DQFEFALTAVAEE (SEQ ID NO:33); DQFEFAL-TAVAEEVNAI (SEQ ID NO:34); FEFALTAVAEEV-NAILKA (SEQ ID NO:35); SKDQFEFALTAVAEEVNA (SEQ ID NO:36); SKDQFEFALTAVAEEVNAILK (SEQ ID NO:37); KVESSPSRSDYI (SEQ ID NO:38); LKVESSPSRSDY (SEQ ID NO:39); KLKVESSPSRSDYI-NAS (SEQ ID NO:40); KVESSPSRSDYINASPIIEHDP (SEQ ID NO:41); or LKVESSPSRSDYINASPII (SEQ ID NO:42).

An "isolated" peptide of the invention is a peptide which either has no naturally-occurring counterpart (e.g., such as an APL), or has been separated or purified from components which naturally accompany it, e.g., in tissues such as pancreas, liver, spleen, ovary, testis, muscle, joint tissue, neural tissue, gastrointestinal tissue, or body fluids such as blood, serum, or urine. Typically, the peptide is considered "isolated" when it is at least 70%, by dry weight, free from the proteins and naturally-occurring organic molecules with which it is naturally associated. Preferably, a preparation of a peptide of the invention is at least 80%, more preferably at least 90%, and most preferably at least 99%, by dry weight, the peptide of the invention. Thus, for example, a preparation of peptide x is at least 80%, more preferably at least 90%, and most preferably at least 99%, by dry weight, peptide x. Since a peptide that is chemically synthesized is, by its nature, separated from the components that naturally accompany it, the synthetic peptide is "isolated."

An isolated peptide of the invention can be obtained, for example, by extraction from a natural source (e.g., from human tissues or bodily fluids); by expression of a recombinant nucleic acid encoding the peptide; or by chemical synthesis. A peptide that is produced in a cellular system different from the source from which it naturally originates is "isolated," because it will be separated from components which naturally accompany it. The extent of isolation or purity can be measured by any appropriate method, e.g., column chromatography, polyacrylamide gel electrophoresis, or HPLC analysis.

As used herein, "protection from a mammalian disease" means prevention of onset of a mammalian disease or lessening the severity of a disease existing in a mammal. "Prevention" can include a delay of onset, as well as a partial or complete block in progress of the disease.

As used herein, "a naturally-processed, diabetes-associated peptide fragment" is a peptide fragment produced by proteolytic degradation of a protein (e.g., insulin, proinsulin, preproinsulin, IA-2, IA-2β:, or GAD65) in an antigen presenting cell of a mammal. Recognition of such a peptide by CD4 T cells of a mammal (e.g., a human patient) is indicative of the existence, or future onset, of diabetes in the mammal.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. Unless otherwise indicated, these materials and methods are illustrative only and are not intended to be limiting. All publications, patent applications, patents and other references mentioned herein are illustrative only and not intended to be limiting.

Other features and advantages of the invention, e.g., methods of identifying peptides that activate pathogenic CD4+ T lymphocyte responses, will be apparent from the following description, from the drawings and from the claims.

DETAILED DESCRIPTION

Figure 1:
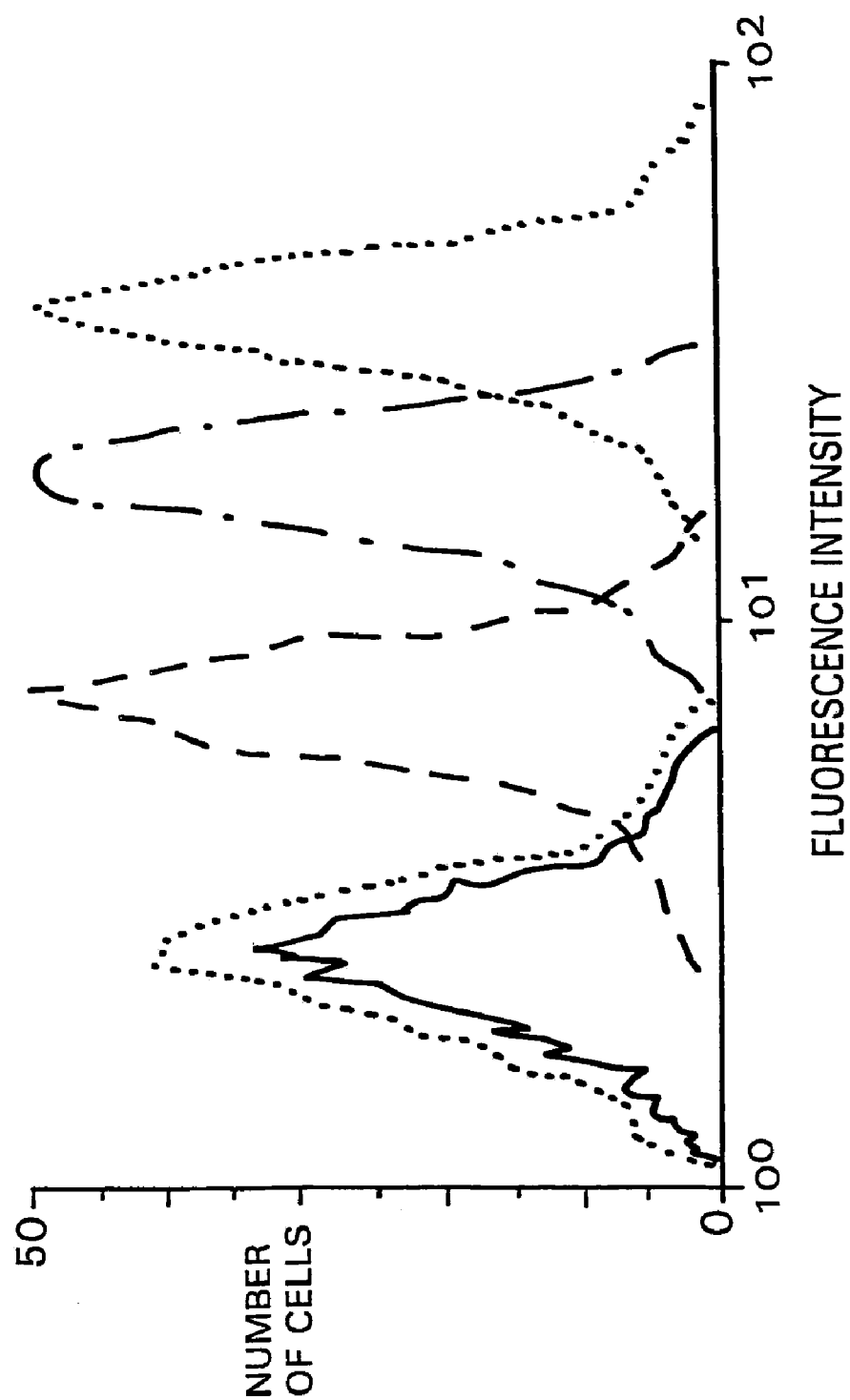
FIG. 1 is a histogram showing the fluorescence-activated flow cytometric profiles of Priess cells that were stained with tetanus toxoid specific rabbit antibody and FITC-conjugated goat antibody-specific for rabbit immunoglobulin at various times after being subjected to the Antigen Delivery System (ADS) using tetanus toxoid as the polypeptide antigen.

The present invention is based on the novel discovery that, by artificially binding a polypeptide of interest (PPI) to the cell membrane of an APC, the APC will transport the PPI to one of the antigen processing organelles within the cell, e.g., endosomes, lysozomes and structures designated "MHC class II compartments" (MIIC) that have lysosomal characteristics and are enriched for class II MHC molecules but are substantially devoid of class I MHC molecules [Peter et al. (1991), Nature 349:669-676]. The PPI is then degraded by proteolytic enzymes into peptide fragments. If any of these peptide fragments has the ability to bind to one of the class II MHC molecules expressed by the individual from which the APC was derived, it will do so in the antigen processing organelle. The resulting peptide-class II MHC molecular complex is then transported to the cell membrane, where it becomes available for interaction with CD4+ T cells bearing antigen specific receptors that specifically recognize that particular peptide-class II MHC complex. By eluting peptides from class II MHC molecules isolated from these APC, a set of naturally processed peptides derived from the PPI, as well as from other polypeptides of intracellular or extracellular origin, is obtained. The peptides, which are specific to the particular class II MHC molecules expressed by the APC, are then chemically separated and their amino acid sequences determined. By comparison of the peptide amino acid sequences to the sequence of the PPI, it is possible to identify those which are derived from the PPI. Thus, the discovery provides a method of identifying peptide fragments that are naturally processed by APC and have intrinsic binding affinity for the relevant class II MHC molecule. The method can be invaluable for identifying peptides derived from a polypeptide suspected of being an antigen that activates CD4+ T cells involved in either (a) the pathogenesis (pathology) of a disease, especially one in which susceptibility or protection is associated with expression of a particular type of class II MHC molecule, or (b) prevention or reduction of the symptoms of a disease, especially one in which protection or a reduction in severity is associated with expression of a particular type of class II MHC molecule. The method is designated "Immunological Mass Fingerprinting."

The described method ensures that the peptides identified are those that both (i) are naturally processed in vivo by the APC, and (ii) become associated, in the APC, with the relevant class II MHC molecules.

Furthermore, the present method controls for class II MHC type, an important aspect essential to link any given peptide to a particular CD4+ T cell-mediated disease in a given individual but especially important in disorders in which class II MHC type determines disease susceptibility or resistance.

Any naturally processed peptide with a sequence that corresponds to a fragment of the PPI, and which binds to a class II MHC molecule associated with the disease of interest, could be a peptide that activates CD4+ T cells that either initiate, promote, or exacerbate the disease or mediate immunity to it. To obtain confirmatory evidence of this possibility, test CD4+ T cells from subjects expressing the relevant class II MHC molecules can be assayed for responsiveness to a peptide identified in accordance with the invention. Control CD4+ T cells can be from subjects also expressing the class II MHC molecule but without symptoms of the disease. A significant response of the test CD4+ T cells and no response of the control CD4+ T cells would indicate that the relevant peptide is involved in the disease process (pathology of the disease) or immunity to the disease. The cellular response phase of the method is designated "Epitope Verification" ("EV").

By applying the methods of the invention to the intracellular portion of the diabetes autoantigen IA-2, IA-2-derived peptides were identified as epitopes that could be involved in the pathogenesis of diabetes in human IDDM patients expressing the DR4 class II MHC allele. Based on their amino acid sequences, these peptides fall into 6 nested groups. A consensus peptide corresponding to the core regions of each nested group was synthesized and tested for its ability to activate CD4+ T cells from either DR4-expressing IDDM patients or DR4-expressing subjects without disease symptoms. Significant responses to at least 1 out of the 6 peptides were detected in peripheral blood lymphocytes of 9/13 DR4-expressing IDDM patients. T cells from none of the control subjects responded to any of the peptides and T cells from 1 of 8 DR4 non-expressing IDDM patients responded to any peptide. These findings suggest that the 6 peptides to which the DR4-expressing IDDM patients responded represent core epitopes capable of binding to DR4 molecules and activating diabetogenic CD4+ T cells in IDDM patients. The ability of all 6 peptides to bind to isolated DR4 molecules was confirmed in an in vitro binding assay.

The methods of the invention can be applied to identifying peptides involved in the pathogenesis of or protection from any of a wide range of diseases, especially those in which relative susceptibility or resistance has been associated with expression of a particular class II MHC allele, provided that the amino acid sequence (or partial amino acid sequence) of a suspect polypeptide antigen is available. Candidate diseases include, without limitation, infectious diseases (e.g., diseases caused by *Chlamydia trachomatis, Helicobacter pylori, Neisseria meningitidis, Mycobacterium leprae, M. tuberculosis*, Measles virus, hepatitis C virus, human immunodeficiency virus, and *Plasmodium falciparum*), cancer (e.g. melanoma, ovarian cancer, breast cancer, colon cancer and B cell lymphomas) [Topalian, S. L. (1994), Curr. Opinion in Immunol. 6: 741-745; Topalian et al. (1996), J. Exp. Med. 183: 1965-1971], and autoimmune diseases (e.g., IDDM, rheumatoid arthritis, multiple sclerosis, myasthenia gravis, and systemic lupus erythamatosus).

The invention also includes the peptides derived from IA-2 using the above method, as described in Example 1. Also included in the invention are APL derived by replacing 1 to 6 (i.e., 1, 2, 3, 4, 5, or 6) amino acid residues of a naturally processed peptide which activates an immune response. Each residue is replaced with a different residue, resulting in an enhanced peptide which still binds to the same class II MHC allele, but elicits qualitatively different responses in CD4+ T cells than does the parent peptide from which the APL is derived. Thus, APL have the potential to be therapeutic and/or prophylactic in diseases in which the CD4+ T cell response to the relevant parent peptide is pathogenic. The invention features methods of therapy and prophylaxis involving the use of APL. The invention also features use of disease-related peptides in the diagnosis of disease or monitoring immune-based therapy.

1. Methods of Identifying CD4+ T Cell Activating Peptide Epitopes Derived from Polypeptide Antigens The methods of the invention have two distinct phases. The first is termed "Immunological Mass Fingerprinting" (IMF) and the second the "Epitope Verification" (EV). The purpose of the IMF is to direct a candidate polypeptide to any one of the antigen processing compartments of an APC where it can be degraded to peptide fragments. Any peptides of the appropriate length (about 9 to 25 amino acid residues), and having specific binding affinity for a particular class II MHC molecule expressed by the APC, will bind to that class II MHC molecule in the antigen processing compartments. The majority of these peptide-class II MHC molecular complexes then migrate to the cell membrane of the APC. The complexes (both cell-membrane associated and intracellular) are isolated from the APC and the peptides eluted from the complexes. The eluted peptides are then separated, their amino acid sequences determined, and the sequences compared to that of the candidate polypeptide.

The IMF can generally be applied to the analysis of peptides produced by an APC expressing defined class II MHC molecules. As such, the method can be useful for basic research studies, e.g., studies aimed at identifying amino acid residues in a polypeptide that determine sites of "cutting" by the proteolytic antigen processing enzymes of APC. Alternatively, where the polypeptide is suspected of being an antigen that activates CD4+ T cells which cause or promote a particular disease or mediate protection from a disease, the IMF can be used to identify disease-related or protective peptide epitopes derived from the polypeptide. This information would be useful for basic research into the etiology of the disease, or as a basis for development of diagnostics, therapeutics, or vaccines for the disease.

A peptide whose amino acid sequence matches that of a region of the candidate polypeptide is likely to be one that activates CD4+ T cells involved in the pathogenesis or immunity to the relevant disease. Such a peptide can be subjected to the EV procedure in which its ability to activate CD4+ T cells from test and control subjects is assayed. Those peptides that activate CD4+ T cells from test subjects but not those from control subjects are identified as peptides that can initiate, promote, or exacerbate the relevant disease or mediate protection from disease or its pathogenic symptoms.

Once such a peptide is identified, it can be synthesized in large amounts, by chemical or recombinant techniques, and used in diagnostic assays similar to the EV procedures listed below. Relevant peptides could be used singly or in combination. Alternatively, expression vectors encoding such a peptide or a combination of such peptides can be used to transfect or transduce appropriate APC (see below), and these can be used in similar diagnostic assays.

Furthermore, multimers (e.g., dimers, trimers, tetramers, pentamers, or hexamers) of a class II MHC molecule containing a peptide defined by the method of the invention, if conjugated with a detectable label (e.g., a fluorescent moiety, a radionuclide, or an enzyme that catalyzes a reaction resulting in a product that absorbs or emits light of a defined wavelength) can be used to quantify T cells from a subject (e.g., a human patient) bearing cell surface receptors that are specific for, and therefore will bind, such complexes. Relatively high numbers of such T cells are likely to be diagnostic of a relevant disease or an indication that the T cells are involved in immunity to the disease. In addition, continuous monitoring of the relative numbers of multimer-binding T cells can be useful in establishing the course of a disease or the efficacy of therapy. Such assays have been developed using tetramers of class I MHC molecules containing an HIV-1-derived or an influenza virus-derived peptide [Altman et al. (1996), Science 274:94-96; Ogg et al. (1998), Science 279:2103-2106], and corresponding class II MHC multimers would be expected to be similarly useful. Such complexes could be produced by chemical cross-linking of purified class II MHC molecules assembled in the presence of a peptide of interest or by modification of already established recombinant techniques for the production of class II MHC molecules containing a single defined peptide [Kazono et al. (1994), Nature 369:151-154; Gauthier et al. (1998), Proc. Natl. Acad. Sci. U.S.A. 95:11828-11833]. The class II MHC molecule monomers of such multimers can be native molecules composed of full-length α and β chains. Alternatively, they can be molecules containing either the extracellular domains of the α and β chains or the α and β chain domains that form the "walls" and "floor" of the peptide-binding cleft.

1.1 IMF

The invention features two different IMF methods, IMF-1 and IMF-2.

1.1.1 IMF-1

In IMF-1, the APC is contacted with a ligand that has an intrinsic ability to bind to a receptor on the surface of APC. Candidate receptor-ligand pairs are described below. Prior to contacting the APC, the ligand is conjugated with biotin. Where the ligand has been produced by recombinant DNA technology, the biotinylation can be performed in the cells (e.g., bacteria) in which the ligand is generated by methods such as those used to biotinylate the polypeptide antigens used in Example 1. Alternatively, the isolated ligand can be biotinylated in vitro by methods known in the art. The ligand will be conjugated with at least one biotin moiety per molecule. It can have 2, 3, 4, 6 or 10 biotin residues per molecule, provided that it retains the ability to bind to the cell surface receptor.

After binding of the biotinylated ligand (b-L) to its receptor on the cell surface, unbound b-L is removed by washing and the APC is contacted with avidin, a polypeptide that binds to biotin. The avidin can be egg avidin or streptavidin. It can also be recombinant avidin containing at least two biotin-binding domains. Native avidin contains 4 biotin binding domains.

After binding of the avidin to the biotin residue(s) on the b-L bound to the surface of the APC, unbound avidin is removed by washing and the APC is contacted with a polypeptide of interest (PPI), also previously conjugated with biotin. Biotinylation of the PPI can be performed by the same methods described for the ligand and the biotinylated PPI (b-PPI) can contain the same number of biotin residues per molecule. However, in order to avoid possible interference with processing, the PPI will preferably contain 1 biotin moiety per molecule.

After binding of the biotinylated PPI (b-PPI) to the avidin on the APC, unbound b-PPI is removed by washing, and the APC is incubated. While the procedure up till this stage is generally performed on ice (i.e., at about 4° C.), the incubation is carried out at 37° C. Alternatively, the incubation may be performed at room temperature (approximately 25° C.) or at a temperature between 25° C. and 37° C. The incubation may be performed for 30 minutes, 1 hour, 2 hours, 3 hours, 4 hours or 6 hours, depending on which gives optimal recovery of peptides. After the incubation, the class II MHC molecules of interest are isolated by any one of various methods known in the art, e.g., immunoprecipitation. Preferably, it is isolated by affinity chromatography using a described method [Gorga et al. (1987), J. Biol. Chem. 262:16087-16094].

Peptides bound non-covalently to the isolated class II MHC molecules are then eluted from them. A variety of methods known in the art can be used. Preferably, the method will be one described previously [Chicz et al. (1992), Nature 358:764-768] and in Example 1 herein.

The eluted peptides are separated by one of a variety of possible chromatographic methods, e.g., reverse phase chromatography. All the resulting fractions that contain peptides are then individually analyzed by matrix assisted laser desorption in time-of-flight (MALDI-TOF) mass spectrometry, using settings that do not fragment the peptides. The peptides corresponding to all the "peaks" obtained on the MALDI-TOF spectrum can then be subjected to individual amino acid sequence analysis. Alternatively, only those peptides corresponding to peaks that are not observed in a control spectrum generated using a sample of peptides obtained by an identical procedure but omitting the step of contacting the APC with b-PPI, can be subjected to amino acid sequence analysis. The sequences of the individual peptides can be obtained by means known to those in the art. They can, for example, be obtained by MALDI-TOF, using instrument settings resulting in the fragmentation of the peptides into small fragments that are analyzed by the mass spectrometer. The amino acid sequences of the peptides are then compared to that of the PPI. Those with a sequence identical to a region of the PPI are candidates for EV.

Alternatively, instead of determining the amino acid sequences of the eluted peptides, "standard" peptides considered to be possible candidates can be subjected to MALDI-TOF mass spectrometry. A test peptide with a peak at the same position in the spectrum as a standard peptide will likely have the same sequence as the standard peptide.

1.1.2 IMF-2

The IMF-2 method is identical to the IMF-1 method except that, instead of contacting the APC with b-L avidin and then with b-PPI, the b-L bound to the APC in IMF-2 is contacted with the PPI conjugated to avidin (av-PPI). Alternatively, the ligand can be conjugated chemically to avidin to give a ligand-avidin complex (L-av). The av-PPI and L-av conjugate can be made chemically by methods known to those in the art. Alternatively, a fusion protein consisting of the PPI and avidin, or of the ligand and avidin, can be made by standard recombinant DNA technology. In either case, the avidin component can be full-length avidin or it can be a fragment of the avidin molecule containing 1, 2, 3, or all 4 biotin-binding domains.

1.2 EV

The EV procedure involves testing of peptides identified by IMF for their ability to bind the class II MHC from which they were eluted and activate various CD4+ T cell populations. Peptides with amino acid sequences either identical to those identified by IMF or corresponding to a core sequence derived from a nested group of peptides identified by the IMF are synthesized. The synthetic peptides are then tested for their ability to bind the class II MHC from which they were eluted and activate CD4+ T cells from (a) test subjects expressing the class II MHC molecule of interest and having at least one symptom of the disease; and (b) control subjects expressing the class II MHC molecule of interest and having no symptoms of the disease. Additional control subjects can be those with symptoms of the disease and not expressing the class II MHC molecule of interest. In some diseases (e.g., those with an autoimmune component) responsiveness in the CD4+ T cells of test subjects but not in CD4+ T cells of the control subjects described in (b) provides confirmatory evidence that the relevant peptide is an epitope that activates CD4+ T cells that can initiate, promote, or exacerbate the relevant disease. In other diseases (e.g., cancer or infectious diseases without an autoimmune component), a similar pattern of responsiveness and non-responsiveness to that described in the previous sentence would indicate that the relevant peptide is an epitope that activates CD4+ T cells that can mediate immunity to the disease or, at least, a decrease in the symptoms of the disease.

Absence of a response in subjects with symptoms of the disease but not expressing the class II MHC molecule provides further evidence for the stated activities of the peptide. On the other hand, a response in such CD4+ T cell would not necessarily exclude such a role but would suggest that the relevant peptide is capable of (i) binding to some MHC class II molecule expressed by the relevant subject; and (ii) being recognized by CD4+ T cells in association with that class II MHC molecule.

CD4+ T cell responses can be measured by a variety of in vitro methods known in the art. For example, whole peripheral blood mononuclear cells (PBMC) can be cultured with and without a candidate synthetic peptide and their proliferative responses measured by, e.g., incorporation of [$^3$H]-thymidine into their DNA. That the proliferating T cells are CD4+ T cells can be tested by either eliminating CD4+ T cells from the PBMC prior to assay or by adding inhibitory antibodies that bind to the CD4+ molecule on the T cells, thereby inhibiting proliferation of the latter. In both cases, the proliferative response will be inhibited only if CD4+ T cells are the proliferating cells.

Alternatively, CD4+ T cells can be purified from PBMC and tested for proliferative responses to the peptides in the presence of APC expressing the appropriate class II MHC molecule. Such APC can be B-lymphocytes, monocytes, macrophages, or dendritic cells, or whole PBMC. APC can also be immortalized cell lines derived from B-lymphocytes, monocytes, macrophages, or dendritic cells. The APC can endogenously express the class II MHC molecule of interest or they can express transfected polynucleotides encoding such molecules. Where the subjects are humans, the APC can also be T cells since human T cells are capable of expressing class II MHC molecules. In all cases the APC can, prior to the assay, be rendered non-proliferative by treatment with, e.g., ionizing radiation or mitomycin-C.

As an alternative to measuring cell proliferation, cytokine production by the CD4+ T cells can be measured by procedures known to those in art. Cytokines include, without limitation, interleukin-2 (IL-2), IFN-γ, IL-4, IL-5, TNF-α, interleukin-3 (IL-3), interleukin-6 (IL-6), interleukin-10 (IL-10), interleukin-12 (IL-12) and transforming growth factor β (TGFβ) and assays to measure them include, without limitation, ELISA, and bio-assays in which cells responsive to the relevant cytokine are tested for responsiveness (e.g., proliferation) in the presence of a test sample. Alternatively, cytokine production by CD4+ lymphocytes can be directly visualized by intracellular immunofluorescence staining and flow cytometry.

Having identified peptide epitopes that are associated with a particular disease, the EV described above can be used as a diagnostic test for the disease. Thus, lymphocytes from a subject suspected of having or being susceptible to the disease can be tested by any of the described methods for a CD4 T lymphocyte response to one or more (e.g., 2, 3, 4, 5, 6, 10, 15, or 20) appropriate peptides. If a significant CD4 T lymphocyte is detected, it is likely that the subject has or will develop the disease. The disease can be, for example, IDDM and the peptides can be derived from, for example, insulin, proinsulin, preproinsulin, GAD65, IA-2, or phogrin. Appropriate peptides can be, for example, any of those listed below (e.g., those with SEQ ID NOS:1-42).

In addition, peptides identified as being associated with any of the diseases listed herein (e.g., an autoimmune disease such as IDDM, MS, or RA) can be used to induce immunological tolerance in lymphocytes (e.g., CD4+ T lymphocytes) associated with the initiation, progress, or pathological symptoms of the disease. Tolerization of these lymphocytes can be useful for prophylaxis against and/or therapy of the relevant disease. Induction of tolerance can be achieved by administering an appropriate peptide to a subject, e.g., a subject having, suspected of having, or being susceptible to any of the autoimmune diseases described herein, e.g., IDDM, MS, or RA. Methods of testing for efficacy of a peptide in inducing tolerance, methods and routes of administration, and doses to be administered are essentially the same as those described below for APL. The peptides can be fragments of any the polypeptides disclosed herein, e.g., insulin, proinsulin, preproinsulin, GAD65, IA-2, or phogrin. They can be, for example, those with SEQ ID NOS: 1-42.

As an alternative to the above-described EV, peptides identified by the IMF can be tested for their ability to bind to an appropriate class II MHC molecule by methods known in the art using, for example, isolated class II MHC molecules or cells transfected with nucleic acid molecules encoding them. One such method is described in Example 2. These binding assays can also be used to test the ability of peptides to bind to alternative class II MHC molecules, i.e., class II MHC molecules other than those from which they were eluted using the IMF method of the invention. The diagnostic methods of the invention using such peptides and therapeutic methods of the invention, using either the peptides or APL derived from them, can-be applied to subjects expressing such alternative class II MHC-molecules.

1.3 Diseases and their Associations with Class II MHC Genes

The methods of the invention can be applied to the analysis of peptides involved in diseases associated with expression of defined class II MHC molecules and in which pathology or protection is due to the action of activated CD4+ T cells. Such diseases include, without limitation, certain infectious diseases, cancer, and autoimmune diseases.

An example of an infectious disease that fulfills the above criteria is human leprosy, which is caused by *Mycobacterium leprae*. The bacteria infect and thrive in peripheral Schwann cells and macrophages. The disease is characterized by depressed cellular immunity but normal antibody responses. Leprosy has been associated with the expression of DRB1 class II MHC molecules in which codon 13 encodes Arg or codons 70 and 71 encode Arg [Zerva et al. (1996), J. Exp. Med. 183: 829-836]. In addition, the ability to spontaneously clear hepatitis C virus is associated with expression of DQ B1*0301 molecules and, since DQB1*0302 is under-represented in hepatitis virus C infected subjects, DQB1*0302 expressing individuals may be protected form infection with the virus [Cramp et al. (1998), J. Hepatol. 29:207-213]. Furthermore, melanoma cell-specific CD4+ T cells, which may be involved in protective immune responses to malignant melanoma, recognize tyrosinase epitopes presented by HLA-DRB1*0401 class II molecules [Topalian et al. (1996), supra]. Other MHC class-II associated diseases are listed above.

Examples of autoimmune diseases to which the methods of the invention can be applied include, without limitation, IDDM, rheumatoid arthritis (RA), multiple sclerosis (MS), systemic lupus erythematosus (SLE), and myasthenia gravis (MG). RA is associated with expression of DRB1 alleles encoding the motifs QKRAA (SEQ ID NO:53), QRRAA (SEQ ID NO:54) or RRRAA (SEQ ID NO:55) at amino residues 70-74 (DRB1*0101, 0401, 0403, 0405). MS is associated with expression of DRB1*1501, DQA1*0102 and DQB1*0602 alleles. SLE is associated with the expression of DRB1*03, DRB1*1501, DQA1*0501 and DQB1*0201 alleles. MG is associated with the expression of DR3 and DQ2 (DQA1*0501-DQB1*0201 and DQA1*0201-DQB1*0201) alleles. Autoimmune ovarian failure is associated with DQB1 genes encoding Asp at position 57. Graves' thyroiditis, Hashimoto's thyroiditis, and primary hypothyroidism all show weak association with the expression of the DR5 and DR3 alleles. Coeliac disease is associated with the expression of HLA-DQA1*0501 and DQB1*0201 alleles. Primary biliary cirrhosis is associated with the expression of DRB1*0801-DQA1*0401/0601-DQB1*04 alleles. Autoimmune hepatitis is associated with the expression of DRB3*0101 or DRB1*0401 alleles. Addison's disease is associated with the expression of DRB1*03, DQA1*0501 and DQB1*0201 alleles. Vitiligo is associated with the expression of DRB1*0701 and DQ2 alleles. Anti-glomerular basement membrane disease (Goodpasture's syndrome) is associated with the expression of DR15 and DR4 alleles.

Pathology in RA, MS, and IDDM is considered to be due predominantly to CD4+ T cell-dependent cell-mediated autoimmune responses, while that of SLE and MG is due predominantly to CD4+ T cell dependent antibody-mediated autoimmune responses. In RA the inflammatory response induced by the activated CD4+ T cells is focused on joint synovia, in MS on neural myelin sheaths, and in IDDM on pancreatic β cells located in the islets of Langerhans. SLE is a systemic autoimmune disease involving multiple organs. The muscle fatigue observed in MG is due to the development in the patient of antibodies that bind to the acetylcholine receptor in neuromuscular junctions.

1.31 IDDM

Diabetes is a syndrome in which levels of blood glucose are abnormally high. Blood glucose levels are normally controlled by the release of the hormone insulin from β cells located in the islets of Langerhans in the pancreas. Type 1 diabetes (IDDM), the class of diabetes relevant to the present application, results from destruction of β cells. The resulting high blood glucose level, if unchecked, leads to dehydration, acid/base disturbances in the blood, brain swelling, coma and death. Treatment with injections of synthetic human insulin restores glucose control. Once initiated, however, this treatment is required for life since β cells do not re-generate. Once established, diabetes is a major burden to the patient, to the patient's family, and to society. Although modern dosages and preparations of insulin can maintain blood glucose within reasonable limits, over several years complications of the disease inevitably occur. The commonest severe complications of diabetes are kidney failure, blindness, and loss of nerve function. In developed countries, diabetes is the single major cause of chronic kidney failure requiring long-term dialysis or transplantation. The life span of a diabetic patient is reduced by an average of 10 years. Being a relatively common disease (IDDM affects 1/200-1/400 of the population), it consumes vast resources; it is estimated that in the developed world the cost of diabetes care is 8% of the acute health services budget.

In light of this background, it is important to consider whether there are ways in which IDDM can be prevented from developing. First, β cell destruction takes place over many months or years until there are too few cells synthesizing insulin (approximately 10% of normal) to sustain normoglycaemia and the patient is diagnosed diabetic. If the process of β cell damage could be halted, IDDM would not develop. Second, it is now possible to predict who will develop IDDM in the future with a high degree of sensitivity (i.e., a good "pick-up" rate) and specificity (a low false positive rate) through simple blood tests. Third, it appears that β cells are destroyed as part of an inadvertent immune response, during which normal components of the cell (proteins called autoantigens) become the target of an autoimmune attack. Several of the major autoantigens from β cells have been identified (see below). Another key characteristic of IDDM is the strong genetic influence on the development of the disease. Although several genes are involved, the most predominant ones are the class II genes of the human MHC, i.e., the human leukocyte antigen (HLA) genes. These genes exert a dominant control over the immune response, by selecting the peptide segments (epitopes) within autoantigens against which a particular individual's immune system focuses its attack. By identifying these epitopes, it will be possible devise strategies to intervene in the development of the disease at a pre-clinical stage. This invention includes a new technique for the accurate identification of such epitopes.

The HLA gene complex is the most polymorphic in the human genome, so the possibility of an individual's expressing different HLA molecules is high. However, in patients with IDDM, a very limited set of the class II HLA genes is strongly associated with the development of the disease. As a result, within a racially defined population, particular class II HLA genes are much more common in diabetics compared with the total population. Below are examples of the HLA class II genes found more commonly in North American and North European IDDM patients, and therefore likely to have a strong contributory role to the development of the disease:
Class II HLA-DR types: DRB1*0401, 0405
Class II HLA-DQ types: DQB1*0302, 0201, 0501; DQA1*0501,0301.

Susceptibility genotypes in Caucasians, Blacks, and Japanese are indicated below:

Caucasians:

DRB1*04, DQA1*0301, DQB1*0302
DRB1*04, DQA1*0301, DQB1*0201
DRB1*03, DQA1*0501, DQB1*0201
Additional susceptibility genotypes in Blacks:

DRB1*09, DRB1*07, DQA1*0301, DQB1*0201
Additional susceptibility genotypes in Japanese:

DRB1*08, DQA1*0301, DQB1*0302
DRB1*09, DQA1*0301, DQB1*0303

A crucial question is: how do HLA class II molecules differ in function between a diabetic possessing HLA-DQA1*0301/DQB1*0302 (DQ8) and a non-diabetic possessing HLA- DQA1*0102/DQB1*0602 (DQ6), which appears to be protective from IDDM? It is known that the different HLA class II molecules select and present different peptide epitopes to T cell receptors. Thus it is probable that a "diabetes promoting" HLA class II molecule selects a peptide epitope in some way that initiates or fosters a dangerous autoimmune response.

In North American and North European IDDM patients, HLA-DRB1*0401 is moderately associated with IDDM, while the DRB1*0405 type has a stronger influence on development of disease. However, a particular group of HLA-DQ molecules contribute the strongest susceptibility. In this group are HLA-DQ molecules that contain an β polypeptide chain with the amino acid arginine at position 52 (arg52α), and a β polypeptide chain with any amino acid other than aspartate at position 57 (non-asp57β). One of the best characterized of these is HLA-DQ8 (see above) which is typically linked to HLA DRB1*0401 (i.e., the two genes are often found together on the same chromosome). These genes confer the highest risk for IDDM [Khalil et al. (1992), Diabetes 41:378-384]. It is estimated that an individual expressing an arg52α/non-asp57β HLA-DQ molecule who has a first degree relative with IDDM has a 1:4 chance of developing IDDM himself; that is 100 times the population risk [Nepom, G. T. (1995), Annu. Rev. Med. 46:17-25].

1.4 Species

The methods of the invention can be applied to diseases with the described characteristics in a wide range of mammalian species, e.g., humans, non-human primates, horses, cattle, pigs, sheep, goats, dogs, cats, rabbits, guinea pigs, hamsters, rats, and mice. They will preferably be applied to diseases of humans.

It is known, for example, that certain mouse strains are susceptible to murine forms of RA, MS, IDDM and SLE. Moreover, in these mice, the susceptibility is associated with the expression of particular class II MHC genes and the tissue damage is due to the action of activated CD4+ T cells or CD4+ T cell dependent antibody responses. For example, the non-obese diabetic (NOD) mouse, which is susceptible to spontaneous IDDM, expresses the H-2A$^{g7}$ molecule, and the susceptibility of NOD mice to IDDM has been linked to the H-2A$^{g7}$ gene. Furthermore, the tissue destruction in NOD IDDM has been shown to be mediated by CD4+ T cells. In addition, susceptibility to collagen-induced arthritis (CIA) in mice has been associated with expression of H-2A$^a$, H-2A$^r$, H-2A$^{w3}$, and H-2A$^{w17}$ class II MHC molecules and the joint pathology in CIA is generally considered to be mediated by CD4+ T lymphocytes.

With respect to cancers, the reticular cell sarcomas of SJL mice are dependent for growth on cytokines produced by activated CD4+ T cells and require the expression of certain class II MHC molecules.

1.5 Class II MHC Molecules

Class II MHC molecules have been identified in multiple mammalian species. In some of these species, expression of a particular class II MHC molecule has been associated with a particular CD4+ T cell-mediated diseases (see above). In humans, for example, the class II MHC molecules are designated HLA-DR, HLA-DQ, and HLA-DP and in mice, H-2A and H-2E. In all species, there are multiple alleles of each gene.

1.6 Antigen Presenting Cells (APC)

APC that can be used for the IMF methods of the invention will be those listed above for use in EV, i.e., B lymphocytes, macrophages, monocytes, dendritic cells, and, in humans, T cells. Alternatively, immortalized lines of such cells can be used.

Ligands that could be used with B lymphocyte APC include lectins such as pokeweed mitogen (PWM); antibodies (or functional fragments of antibodies such as Fab, F(ab')$_2$ or Fv fragments) that bind to APC surface receptors that are components of the cellular machinery for internalization and presentation of antigen, or are involved in signalling for antigen internalization, e.g., complement receptors (CD21, CD35, CD11b/CD18, CD11c/CD18), the B cell receptor complex (including immunoglobulin molecules), mannose receptors, CD19, CD22, CD40, CD20, and CD45; ligands for the above listed receptors on B cells (e.g., soluble CD40 ligand) and other APC; and whole Ig molecules of either irrelevant specificity or with the ability to bind to the PPI or a tag (e.g., a peptide or hapten) conjugated to the PPI or fragments of such molecules that include the Fc portion and thus can bind to Fc receptors in APC cell membranes.

Receptors to which the above ligands bind are as follows. PWM, which is derived from *Phytolacca americana*, binds to a number of carbohydrate moieties. It binds selectively to disulfide-linked members of the Ig family of proteins e.g., the surface Ig molecules that constitute the antigen specific receptors of B lymphocytes. Any molecule on the surface of B cells to which PWM can bind will be a receptor for PWM. Lectins that could be used instead of PWM include the following carbohydrate binding molecules: pea lectin, concanavalin A, lentil lectin, phytohemagglutinin (PHA) from *Phaseolus vulgaris*, peanut agglutinin, soybean agglutinin, Ulex europaeus agglutinin-I, Dolichos biflorus agglutinin, Vicia villosa agglutinin and Sophora japonica agglutinin. The receptors for antibodies or ligands that bind APC surface receptors will, by definition, be the receptors themselves, examples of which are listed above. Receptors for Ig molecules of irrelevant specificity or with the ability to bind to the PPI or a tag conjugated to the PPI, or fragments of such molecules that include Fc portions, are Fc receptors on B lymphocytes, macrophages, and monocytes.

1.7 Polypeptide Antigens

Polypeptide antigens that can be used with the IMF methods can be those with a known amino acid sequence or those in which at least part of the amino acid sequence is known. They can be polypeptides that themselves are known or suspected to be involved in the disease process (e.g., IA-2 in IDDM) or they can be derived from microbial organisms known or suspected to be involved in the disease process (e.g., *M. leprae* in leprosy). Examples of other polypeptide antigens include the core and viral coat proteins of viruses such as hepatitis C virus, the heat shock proteins of mycobacteria, and tyrosinase in melanoma. Furthermore, the polypeptide antigen can be the full-length protein or it can be a fragment of the protein known or suspected to be involved in the disease process (e.g., the intracellular portion of IA-2 in IDDM).

Examples of polypeptides that are suspected autoantigens in MS (including murine experimental autoimmune encephalomyelitis) are myelin basic protein (MBP), proteolipid protein (PLP), myelin oligodendrocyte protein (MOG), and alpha B-crystallin. Collagen is considered to be an autoantigen in RA, the acetylcholine receptor in MG, and Smith protein, RNP ribonucleoprotein, and SS-A and SS-B proteins in SLE. Other autoimmune disease and polypeptides that have been implicated as autoantigens involved in their genesis are listed below:

Autoimmune ovarian failure: 3β hydroxysteroid dehydrogenase
Graves' thyroiditis: thyroglobulin, thyroid peroxidase, and thyroid stimulating hormone receptor
Hashimoto's thyroiditis: thyroglobulin and thyroid peroxidase
Primary hypothyroidism: thyroglobulin and thyroid peroxidase
Coeliac disease: transglutaminase
Primary biliary cirrhosis: pyruvate dehydrogenase
Autoimmune hepatitis: cytochrome P4502D6
Addison's disease: 21α hydroxylase
Vitiligo: tyrosinase
Anti-glomerular basement membrane disease (Goodpasture's syndrome): type IV collagen
Systemic sclerosis: Scl-70

A more detailed description of autoantigens suspected to be involved in IDDM is provided below.

The inappropriate autoimmune response that leads to IDDM targets proteins in the pancreatic β cell. There are several autoantigens that have been associated with IDDM, of which 3 are considered to be the major ones: insulin/proinsulin; glutamic acid decarboxylase (65 kD isoform; GAD-65); and IA-2. The term "major" here is used to denote the fact that: (a) most (i.e., 80-90%) IDDM patients make an immune response to at least one of these 3; and (b) in the prediction of IDDM in high risk individuals, an immune response to all 3 autoantigens carries a very strong risk of future IDDM.

Insulin is synthesized initially as pre-proinsulin (106 amino acids), and the molecule resulting from cleavage of the leader sequence is designated proinsulin. Proinsulin (82 amino acids) is a single polypeptide looped back upon itself by 2 intra-chain disulfide bonds. The C chain (also called C-peptide, 31 amino acids) of proinsulin is cleaved to give the secreted form of insulin which comprises two chains (A, 30 amino acids long, and B, 21 amino acids long) joined by the 2 disulfide bonds.

Spontaneously arising antibodies to insulin (insulin autoantibodies, IAA) were first identified in untreated newly diagnosed diabetic patients in 1983 [Palmer et al. (1983), Science 222:1337-1339]. Typically, 40-50% of young IDDM or pre-IDDM patients have IAA, while they are rarer in adolescents and adults. Insulin autoantibodies have been shown to react equally well with human, porcine, bovine, rat, sheep and chicken insulin but they fail to react with isolated A or B insulin chains [Castano, L. and Eisenbarth, G.S. (1990), Annu. Rev. Immunol. 8:647-79] suggesting that both chains contribute to form the epitope(s) of these autoantibodies. Recent work has provided more evidence for the involvement of both A and B chains in epitope generation, suggesting that a 6 amino acid sequence in the A chain and a 3 amino acid sequence in the B chain are included in the epitopes recognized by insulin autoantibodies; this region differs from the insulin receptor binding domain [Castano et al. (1993), Diabetes 42:1202-1209]. Autoantibodies to proinsulin can be detected in 22% of prediabetic patients before the onset of type 1 diabetes [Kuglin et al. (1990), Diabet. Med. 7:310-314].

Baekkeskov and co-workers showed that more than 80% of newly diagnosed diabetic children had autoantibodies to a β cell autoantigen of 64 kDa relative molecular mass [Baekkeskov et al. (1982), Nature 298:167-169], and autoantibodies were also present in relatives at high risk of future diabetes onset [Baekkeskov et al. (1987), J. Clin. Invest. 79:926-934; Atkinson et al. (1990), Lancet 335:1357-60]. The molecular identification of the 64 kDa antigen as GAD was made in 1990 [Baekkeskov et al. (1990), Nature 347:151-156]. GAD is an enzyme involved in synthesis of the inhibitory neurotransmitter γ-amino butyric acid and probably has a role in signaling for insulin release. There are two isoforms of the enzyme: GAD65 and GAD67. By far the major representative in human islets of Langerhans is GAD65. Autoantibodies to GAD65 are present in the serum of 70-80% of patients with new onset IDDM [Petersen et al. (1994), Diabetes 43:459-467]. Like IAA, GAD autoantibodies are an early predictive marker of the disease, associated with high risk for development of IDDM. They are present in over 80% of individuals known to be at high risk of developing IDDM because of a family history and the presence of immune markers [De Aizpurua et al. (1992), Proc. Natl. Acad. Sci. U.S.A. 89:9841-9845; Seissler et al. (1993), J. Clin. Invest. 92:1394-1399].

In early immunoprecipitation experiments, mild trypsin treatment of a 64 kDa islet cell protein resulted in the formation of 40 kDa and 37 kDa protein fragments which bind autoantibodies present in the sera of patients with IDDM [Christie et al. (1990), J. Exp. Med. 172:789-794]. Most importantly, autoantibodies to these fragments were shown to be highly predictive of IDDM in at-risk individuals [Christie et al. (1994), Diabetes 43:1254-1259]. The molecular targets of these autoantibodies have now been identified. The 40 kDa fragment is a component of IA-2, also confusingly called ICA512 [Payton et al. (1995), J. Clin. Invest. 96:1506-1511; Bonifacio et al. (1995), J. Immunol. 155:5419-5426; and Rabin et al. (1994), J. Immunol. 152:3183-3188]. Subsequently, the 37 kDa fragment was identified as phogrin (IA-2β), a tyrosine phosphatase which shares 85% homology with IA-2. Autoantibodies to IA-2 and phogrin appear during the prediabetic period [Bonifacio et al. (1998), J. Immunol. 161: 2648-2654] and are highly predictive of IDDM development in at-risk individuals. IA-2 is synthesized as a large protein of 106 kDa which has an intracellular domain at residues 603-1055. The intracellular domain of IA-2 is the target of almost all autoantibody reactivity to IA-2 [Kawasaki et al. (1997), J. Clin. Endocrinol. Metab. 82:375-80].

2. Peptides

Peptides of the invention include peptides that bind to class II MHC molecules and activate CD4+ T cells involved in a disease process or protection from a disease. The class II MHC molecule can be a class II MHC molecule that is associated with susceptibility or resistance to a disease. Diseases can be any of the diseases cited herein and the species from which the peptides are obtained can be any of those cited herein. The class II MHC molecules are preferably human class II HLA molecules, i.e., DR, DP or DQ molecules. They can be, for example, peptides that bind to DR4 or DQ8 molecules. The polypeptides from which the peptides of the invention are derived can be any of those cited herein. The peptides generally are 9 to 30 (e.g., 13 to 25) amino acids in length. Polypeptides and class II MHC molecules can be from any the species listed herein and the disease can be a disease of any of those species.

The peptides can be derived, for example, from IA-2 and can bind to HLA-DR4 molecules. The peptides can be, for example, any one of the following peptides:
VSSQFSDAAQASPSS (SEQ ID NO:1); SVSSQFSDAAQASPS (SEQ ID NO:2); SSVSSQFSDAAQASP (SEQ ID NO:3); SVSSQFSDAAQASPSSHSS (SEQ ID NO:4); SRVSSVSSQFSDAAQASPSSHSST (SEQ ID NO:5); SVSSQFSDAAQASPSSHSSTPSWC (SEQ ID NO:6); VSSQFSDAAQASPSSHSSTPSWCE (SEQ ID NO:7); VSSVSSQFSDAAQASPSSHSS (SEQ ID NO:8); TQETRTLTQFHF (SEQ ID NO:9); YLKNVQTQETRTL (SEQ ID NO:10); VQTQETRTLTQFHF (SEQ ID NO:11); LKNVQTQETRTLTQF (SEQ ID NO:12); YLKNVQTQETRTLTQ (SEQ ID NO:13); KNVQTQETRTLTQFH (SEQ ID NO:14); SFYLKNVQTQETRTLTQFH (SEQ ID NO:15); FYLKNVQTQETRTLTQFHF (SEQ ID NO:16); AYQAEPNTCATAQ (SEQ ID NO:17); LCAYQAEPNTCATAQG (SEQ ID NO:18); LAKEWQALCAYQAEPNT (SEQ ID NO:19); AYQAEPNTCATAQGEGNIK (SEQ ID NO:20); WQALCAYQAEPNTCATAQ (SEQ ID NO:21); LAKEWQALCAYQAEPNTCATAQGE (SEQ ID NO:22); GCTVIVMLTPLVED (SEQ ID NO:23); CTVIVMLTPLVEDG (SEQ ID NO:24); ESGCTVIVMLTPLVEDG (SEQ ID NO:25); MVWESGCTVIVMLTPL (SEQ ID NO: 26); SGCTVIVMLTPLVEDGVK (SEQ ID NO:27); ESGCTVIVMLTPLVEDGV (SEQ ID NO:28); WQMVWESGCTVIVMLT (SEQ ID NO:29); DFWQMVWESGCTVIVMLT (SEQ ID NO:30); FWQMVWESGCTVIVMLTPLV (SEQ ID NO:31); MVWESGCTVIVMLTPLVEDGV (SEQ ID NO:32); DQFEFALTAVAEE (SEQ ID NO:33); DQFEFALTAVAEEVNAI (SEQ ID NO:34); FEFALTAVAEEVNAILKA (SEQ ID NO:35); SKDQFEFALTAVAEEVNA (SEQ ID NO:36); SKDQFEFALTAVAEEVNAILK (SEQ ID NO:37); KVESSPSRSDYI (SEQ ID NO:38); LKVESSPSRSDY (SEQ ID NO:39); KLKVESSPSRSDYINAS (SEQ ID NO:40); KVESSPSRSDYINASPIIEHDP (SEQ ID NO:41); and LKVESSPSRSDYINASPII (SEQ ID NO:42).

The peptides can be prepared using the described IMF methodologies. Smaller peptides (less than 50 amino acids long) can also be conveniently synthesized by standard chemical means. In addition, both polypeptides and peptides can be produced by standard in vitro recombinant DNA techniques, synthetic techniques, and in vivo recombination/genetic recombination, using the nucleotide sequences encoding the appropriate polypeptides or peptides. Methods well known to those skilled in the art can be used to construct expression vectors containing relevant coding sequences and appropriate transcriptional/translational control signals. See, for example, the techniques described in Maniatis et al., Molecular Cloning: A Laboratory Manual [Cold Spring Harbor Laboratory, N.Y., 1989], and Ausubel et al., Current Protocols in Molecular Biology, [Green Publishing Associates and Wiley Interscience, N.Y., 1989].

A variety of host-expression vector systems can be used to express the peptides and polypeptides. Such host-expression systems represent vehicles by which the polypeptides of interest can be produced and subsequently purified, but also represent cells that can, when transformed or transfected with the appropriate nucleotide coding sequences, produce the relevant peptide or polypeptide in situ. These include, but are not limited to, microorganisms such as bacteria, e.g., E. coli or B. subtilis, transformed with recombinant bacteriophage DNA, plasmid or cosmid DNA expression vectors containing $TR_{1-41}$ peptide coding sequences; yeast, e.g., Saccharomyces or Pichia, transformed with recombinant yeast expression vectors containing the appropriate coding sequences; insect cell systems infected with recombinant virus expression vectors, e.g., baculovirus; plant cell systems infected with recombinant virus expression vectors, e.g., cauliflower mosaic virus (CaMV) or tobacco mosaic virus (TMV), or transformed with recombinant plasmid expression vectors, e.g., Ti plasmids, containing the appropriate coding sequences; or mammalian cell systems, e.g., COS, CHO, BHK, 293 or 3T3, harboring recombinant expression constructs containing promoters derived from the genome of mammalian cells, e.g., metallothionein promoter, or from mammalian viruses, e.g., the adenovirus late promoter or the vaccinia virus 7.5K promoter.

3. APL

An altered peptide ligand (APL) is a variant peptide in which 1-6 (i.e., 1, 2, 3, 4, 5, or 6) amino acid residues of a parent wild-type peptide that activates a response in CD4+ T cells have been changed. In an APL of the invention, less than 50%, less than 40%, less than 30%, less than 25%, less than 20%, less than 15%, less than 10%, or less than 5% of amino acid residues of the present wild-type peptide can be changed. Thus, for example, in an APL derived from a wild-type peptide 20 amino acids long and differing from the wild-type peptide at 6 positions, 30% of the amino acids of the wild-type peptide are changed. Alternatively, in an APL derived from a wild-type peptide 15 amino acids long and differing from the wild-type peptide at 3 positions, 20% of the amino acids of the wild-type peptide are changed.

An APL retains at least some ability to bind to the class II MHC molecule to which the parent peptide binds and at least some ability to be recognized by the antigen-specific T lymphocyte receptor(s) of the CD4+ T cell(s) that recognize the parent peptide bound to the appropriate class II MHC molecule. However, the APL activates a response in the CD4+ T cells that is qualitatively different from that activated by the parent peptide. For example, while the parent peptide can activate a helper T cell 1—(Th1-)type response in which the cytokines interleukin-2 (IL-2), interferon-γ (IFN-γ), and tumor necrosis factor-α (TNF-α) are produced by the activated CD4+ T cells, an APL derived from this parent peptide might instead activate a helper T cell 2—(Th2-)type response in the CD4+ T cells. In a Th2 response, the cytokines interleukin-4 (IL-4), interleukin-5 (IL-5), and interleukin-10 (IL-10) are produced by the activated CD4+ T cells. Alternatively, if a particular parent peptide elicits a Th2 response in a given CD4+ T cell, an APL derived from the parent peptide could activate a Th1 response in the T cell. Some APL have been shown to switch a Th1 response to a Th0 response in which both Th1- and Th2-type cytokines are produced. Furthermore, an APL could redirect a CD4+ T cell response towards a Th3-type response in which the predominant cytokine produced is transforming growth factor-β (TGF-β). TGF-β has been shown to be suppressive of a wide range of immune responses.

In general, Th1 responses are associated with cell-mediated immune responses and Th2 responses are associated with antibody—(i.e., B cell-)mediated immune responses. Thus, the relative number of CD4+ T cells responding in a Th1 versus a Th2 type fashion will determine the nature (cell-mediated versus antibody mediated) of the immune response generated by an antigen in a particular individual.

Some conditions, and in particular autoimmune diseases (e.g., RA, IDDM, and MS), have been shown to be due to cellular immune responses and thus to be dependent on Th1 CD4+ T cell responses. Other diseases (e.g., MG and SLE) have been shown to be mediated by antibody (i.e., B-cell) responses, and thus to be dependent on Th2 CD4+ T cell responses. Thus, an APL that serves to direct a CD4+ T cell response from a Th1 to a Th2 response can be useful in treatment or prevention of the first category of diseases and an APL that serves to direct a CD4+ T cell response in a Th2 to Th1 direction can be useful in the treatment or prevention of the second category of diseases.

The amino acid substitutions in APL can be radical. For example, an amino acid with a positively charged side chain (e.g., lysine) can be replaced by an amino acid with a negatively charged side chain (e.g., aspartic acid) or a hydrophobic side chain (e.g., isoleucine) and vice versa. In addition, an amino acid with a bulky side chain (e.g., tryptophan) can be replaced with an amino acid with small side chain (e.g., glycine or alanine) and vice versa. Alternatively, the substitutions can be conservative. For example, a negatively charged amino acid can be replaced with another negatively charged amino acid (e.g., aspartic acid with glutamic acid) or one hydrophobic amino acid with another hydrophobic amino acid (e.g., leucine with valine or isoleucine).

Methods to test whether a given APL elicits a predominantly Th1, Th2, Th3, or Th0 response are known in the art. In brief, an APL of interest can be administered to a test subject (e.g., a mouse) expressing a class II MHC molecule of interest (e.g., a human class II MHC molecule) by any one of a variety of routes, e.g., intramuscular, intravenous, subcutaneous, intradermal, intraperitoneal, intrarectal, intravaginal, intranasal, intragastric, intratracheal, or intrapulmonary. In addition, administration can be oral or transdermal, employing a penetrant such as a bile salt, a fusidic acid or another detergent. The injections can be single or multiple (e.g., 2-, 3-, 4-, 6-, 8-, or 10- fold). The peptide can be administered in a physiologically acceptable solution (e.g., a saline solution) and can be administered with or without an adjuvant (e.g., Freund's complete or incomplete adjuvant or cholera toxin). After immunization, the animal can be challenged with the APL, either in vivo or in vitro, by methods known in the art, and the levels of individual cytokines produced measured. In the case of an in vivo challenge, the cytokine secreted into the blood or some other bodily fluid (e.g., urine, saliva, or semen) or lavage (e.g., nasal, pulmonary, rectal, gastric, or vaginal lavages) can be measured. Alternatively, lymphoid cells can be isolated from the animal after challenge and the level of cytokines produced by the cells can be tested, e.g., by culturing and measurement of cytokine levels in culture supernatant by, e.g., ELISA. Isolated lymphoid cells can also be tested for relative numbers of cells producing the cytokines by assays such as the ELISPOT assay or fluorescence analysis following intracellular staining with one or more cytokine binding antibodies, each conjugated with a different fluorophore which emits light of a distinct wavelength. Fluorophores fluorescing at different wavelengths (i.e., colors) are known in the art. Using such fluorescence assays, it is possible to ascertain the range of cytokines being produced by a single cell. If the lymphoid cells are challenged in vitro, assays such as the ELISPOT assay or ELISA can also be used. Should immunization and challenge with an APL result in relatively low levels of IL-2, IFN-β, and TNF-α and relatively high levels of IL-4, IL-5, and IL-10, while immunization and challenge with the parental peptide results in the inverse pattern, the conclusion would be that the APL is useful for switching a response from a Th1 to a Th2 pattern of cytokine production. Where the Th1 response is pathogenic, treatment with the APL can be therapeutic or prophylactic. Similarly, APL and their parent peptides can be tested for their relative abilities to shift a response from a Th2 type response to a Th1 type response, or from a Th1-type response to a Th0- or a Th3-type response.

APL can also be tested by any of the protocols in human volunteers. Alternatively, lymphoid cells could be isolated from a subject (e.g., a human subject) and both immunized and challenged in vitro. In addition, APL can be administered to "SCID-Hu" mice, which are mice genetically deficient in murine T and B lymphocytes and reconstituted with human lymphoid cells. Due to the inherent immunological deficiency in these animals, the human lymphoid cells are not rejected and will engraft. After immunizing and challenging these mice with an APL (using any of methodologies described above), their cytokine responses can be measured by any of the methods described above. To ensure that the cytokines detected in the assays are human origin, human species-specific reagents (e.g., antibodies) can be used for the assays (e.g., ELISA or ELISPOT). Furthermore, in order to exclude presentation of the APL to human CD4+ T cells by murine class II MHC molecules, SCID mice could be bred with class II MHC "knockout" mice in order to generate mice deficient in both lymphocytes and class II MHC molecules. By reconstituting the resulting mice with human lymphoid cells, a SCID-Hu mouse is provided in which essentially the only CD4+ T cells capable of responding are human CD4+ T cells and the only class II MHC molecules capable of presenting the APL are human class II MHC molecules on the surface of human lymphoid cells. Alternatively, the recipient of human lymphoid cells could be a hybrid mouse derived by breeding SCID mice with DR (e.g., DR4) or DQ (e.g., DQ8) transgenic mice made on a class II MHC knockout background. Again the only class II MHC molecules present would be the human DR or DQ molecules contributed by the transgenic parental mice.

RAG-1 deficient mice can be used instead of the SCID mice for generation of the described human mouse chimeric animals. RAG-1 deficient mice, like SCID mice, lack T and B lymphocytes but have the advantage that the relevant mutation is not "leaky." Thus, while late in life SCID mice can develop a low number of lymphocytes, this does not occur in RAG-1 deficient mice.

The APL of the invention can be obtained by any of the methods described above for peptides and polypeptides. APL of the invention also include those described above, but modified for in vivo use by the addition, at either or both the amino- and carboxyl-terminal ends, of a blocking agent to facilitate survival of the relevant peptide in vivo. This can be useful in those situations in which the peptide termini tend to be degraded by proteases prior to cellular or mitochondrial uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptides can be covalently or noncovalently coupled to pharmaceutically acceptable "carrier" proteins prior to administration.

Also of interest are peptidomimetic compounds that are designed based upon the amino acid sequences of the APL. Peptidomimetic compounds are synthetic compounds having a three-dimensional conformation (i.e., a "peptide motif") that is substantially the same as the three-dimensional conformation of a selected peptide. The peptide motif provides the peptidomimetic compound with the ability to activate CD4+ T cells in a manner qualitatively identical to that of the APL from which the peptidomimetic was derived. Peptidomimetic compounds can have additional characteristics that enhance their therapeutic utility, such as increased cell permeability and prolonged biological half-life.

The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

4. Methods of Therapy Using APL

An APL that has the ability to elicit a cytokine response in CD4+ T cells that is non-pathogenic and/or is suppressive of a pathogenic CD4+ T cell cytokine response elicited by the APL's parental peptide, could be useful in therapy, palliation, or prophylaxis of a disease caused by the pathogenic CD4+ T lymphocyte response to the parental peptide.

For example, if "peptide x" elicits a potent Th1-type diabetogenic response in CD4+ T cells in a patient with a HLA-DR4, DQ8 haplotype, treatment of the patient with an APL derived from peptide x that elicits a Th2 CD4+ T cell response can be therapeutic or palliative in that patient. Alternatively, if the patient is prediabetic, treatment with the APL could prevent or delay the onset of clinical disease.

These methods of the invention fall into 2 basic classes, i.e., those using in vivo approaches and those using ex vivo approaches.

4.1 In Vivo Approaches

In one in vivo approach, the APL (peptide or peptidomimetic) itself is administered to the subject by any of the routes listed above. It is preferably delivered directly to an appropriate lymphoid tissue (e.g. spleen, lymph node, or mucosal-associated lymphoid tissue (MALT)).

The dosage required depends on the choice of APL, the route of administration, the nature of the formulation, the nature of the patient's illness, and the judgment of the attending physician. Suitable dosages are in the range of 0.1-100.0 µg/kg. Wide variations in the needed dosage are to be expected in view of the variety of APL available and the differing efficiencies of various routes of administration. For example, oral administration would be expected to require higher dosages than administration by i.v. injection. Variations in these dosage levels can be adjusted using standard empirical routines for optimization as is well understood in the art.

Alternatively, a polynucleotide containing a "minigene" encoding the APL can be delivered to an appropriate cell of the animal. Expression of the minigene will preferably be directed to lymphoid tissue of the subject by, for example, delivery of the polynucleotide to the lymphoid tissue. This can be achieved by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1-10 µm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 µm and preferably larger than 20 µm). Microparticles useful for nucleic acid delivery, methods for making them, and methods of use are described in greater detail in U.S. Pat. No. 5,783,567, incorporated herein by reference in its entirety.

Another way to achieve uptake by APLs is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), J. Mol. Med. 73:479]. Alternatively, lymphoid tissue specific targeting can be achieved by the use of lymphoid tissue-specific transcriptional regulatory elements (TRE) such as a B lymphocyte, T lymphocyte, or, optimally, dendritic cell specific TRE. Lymphoid tissue specific TRE are known [Thompson et al. (1992), Mol. Cell. Biol. 12:1043-1053; Todd et al. (1993), J. Exp. Med. 177:1663-1674; Penix et al. (1993), J. Exp. Med. 178:1483-1496].

In the relevant polynucleotides (e.g., expression vectors) the nucleic acid sequence encoding an APL of interest with an initiator methionine and optionally a trafficking sequence is operatively linked to a promoter or enhancer-promoter combination.

Short amino acid sequences can act as signals to target proteins to specific intracellular compartments. For example, hydrophobic signal peptides (e.g., MAISGVPVLGFFIIAV-LMSAQESWA (SEQ ID NO:43)) are found at the amino terminus of proteins destined for the ER. While the sequence KFERQ (SEQ ID NO:44) (and other closely related sequences) is known to target intracellular polypeptides to lysosomes, other sequences (e.g., MDDQRDLISNNEQLP (SEQ ID NO:45) target polypeptides to endosomes. In addition, the peptide sequence KDEL (SEQ ID NO:46) has been shown to act as a retention signal for the ER. Each of these signal peptides, or a combination thereof, can be used to traffic the APL of the invention as desired. For example, a construct encoding a given APL linked to an ER-targeting signal peptide would direct the peptide to the ER, where it would bind to the class II MHC molecule as it is assembled, preventing the binding of intact Invariant Chain (Ii) which is essential for trafficking. Alternatively, a construct can be made in which an ER retention signal on the APL would help prevent the class II MHC molecule from ever leaving the ER. If instead an APL of the invention is targeted to the endosomic compartment, this would ensure that large quantities of the APL are present when replaced by processed peptides, thereby increasing the likelihood that the peptide incorporated into the class II MHC complex is the APL of the invention rather than another naturally-occurring, irrelevant peptide. The likelihood of APL being available for incorporation into class II MHC can be increased by linking the APL to an intact Ii polypeptide sequence. Since Ii is known to traffic class II MHC molecules to the endosomes, the hybrid Ii would carry one or more copies of the APL along with the class II MHC molecule; once in the endosome, the hybrid Ii would be degraded by normal endosomal processes to yield both multiple copies of the APL or molecules similar to it, and an open class II MHC peptide binding cleft. DNAs encoding APL containing targeting signals will be generated by PCR or other standard genetic engineering or synthetic techniques. Trafficking sequences are described in greater detail in U.S. Pat. No. 5,827,516 incorporated herein by reference in its entirety.

A promoter is a TRE composed of a region of a DNA molecule, typically within 100 nucleotide pairs upstream of the point at which transcription starts. Enhancers provide expression specificity in terms of time, location, and level. Unlike a promoter, an enhancer can function when located at variable distances from the transcription site, provided a promoter is present. An enhancer can also be located downstream of the transcription initiation site. The coding sequence of the expression vector is operatively linked to a transcription terminating region. To bring a coding sequence under the control of a promoter, it is necessary to position the translation initiation site of the translational reading frame of the peptide or polypeptide between one and about fifty nucleotides downstream (3') of the promoter.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles which are suitable for administration to a human, e.g., physiological saline. A therapeutically effective amount is an amount of the polynucleotide which is capable of producing a medically desirable result in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This dose can be repeatedly administered, as needed. Routes of administration can be any of those listed above.

4.2 Ex Vivo Approaches

In one ex vivo approach, lymphoid cells, including CD4+ T lymphocytes, are isolated from the subject and exposed to the APL in vitro. The lymphoid cells can be exposed once or multiply (e.g., 2, 3, 4, 6, 8, or 10 times). The pattern of cytokine production by the lymphoid cells can be tested after one or more exposures. Once the desired cytokines are being produced by the lymphoid cells, they are reintroduced into the subject via any of the routes listed herein. The therapeutic or prophylactic efficacy of this ex vivo approach is dependent on the ability of the ex vivo APL activated lymphocytes to actively suppress a pathogenic CD4+ T cell response to the parental wild-type peptide. The potential value of such an approach is indicated by experiments in which CD4+ T cells producing Th2-(or Th0- or Th3-)type cytokines actively suppressed ongoing Th1 responses and disease caused by such Th1 responses [Nicholson and Kuchroo, Curr. Opinion in Immunol. 8:837-842, (1996)].

An alternative ex vivo strategy can involve transfecting or transducing cells obtained from the subject with a polynucleotide containing the APL-encoding minigenes described above. The transfected or transduced cells are then returned to the subject. While such cells would preferably be lymphoid cells, they could also be any of a wide range of types including, without limitation, fibroblasts, bone marrow cells, macrophages, monocytes, dendritic cells, epithelial cells, endothelial cells, keratinocytes, or muscle cells in which they act as a source of the APL for as long as they survive in the subject. The use of lymphoid cells would be particular advantageous in that such cells would be expected to home to lymphoid tissue (e.g., lymph nodes or spleen) and thus the APL would be produced in high concentration at the site where they exert their effect, i.e., activation of an immune response. By using this approach, as in to the above-described in vivo approach using APL encoding polynucleotides, active in vivo immunization with the APL is achieved. The same genetic constructs and trafficking sequences described for the in vivo approach can be used for this ex vivo strategy.

The ex vivo methods include the steps of harvesting cells from a subject, culturing the cells, transducing them with an expression vector, and maintaining the cells under conditions suitable for expression of the APL. These methods are known in the art of molecular biology. The transduction step is accomplished by any standard means used for ex viva gene therapy, including calcium phosphate, lipofection, electroporation, viral infection, and biolistic gene transfer. Alternatively, liposomes or polymeric microparticles can be used. Cells that have been successfully transduced are then selected, for example, for expression of the minigene or of a drug resistance gene. The cells may then be lethally irradiated (if desired) and injected or implanted into the patient.

These methods of the invention can be applied to any of the diseases and species listed here. Methods to test whether an APL is therapeutic for or prophylactic against a particular disease can be simple modifications of the above-described methods for establishing the type of CD4+ T lymphocyte response elicited by a particular APL. Where a therapeutic effect is being tested, a test population displaying symptoms of the disease (e.g., IDDM patients) is treated with a test APL, using any of the above described strategies. A control population, also displaying symptoms of the disease, is treated, using the same methodology, with a placebo. Disappearance or a decrease of the disease symptoms in the test subject would indicate that the APL was an effective therapeutic agent.

By applying the same strategies to subjects prior to onset of disease symptoms (e.g., prediabetic patients considered to likely candidates for IDDM development or experimental animals in which an appropriate disease can be deliberately induced, e.g., experimental autoimmune encephalomyelitis), APL can be tested for efficacy as prophylactic agents, i.e., vaccines. In this situation, prevention of onset of disease symptoms is tested.

The following examples are meant to illustrate, not limit, the invention.

EXAMPLES

Materials and Methods

Culture of Epstein-Barr Virus (EBV) Transformed B Cell Lines. EBV transformed B lymphocyte lines were propagated in RPMI 1640 medium supplemented with glutamine, penicillin/streptomycin and 10% fetal calf serum (FCS) in 50-100 175 cm$^2$ flasks to achieve high volumes of cells. The EBV transformed cells used were Priess cells which are homozygous for the IDDM-permissive DRB1*0401, DRB4*0101 [DR4/DRw53], DQA1*0301/DQB1*0302 [DQ8] HLA genotype. Approximately 50% of cells were harvested every 2-3 days by pelleting, washed with Hanks balanced salts solution (HBSS), counted, resuspended in HBSS, and used for the IMF procedure.

Biotinylated Polypeptide Antigens. Recombinant antigens were generated in *E. coli*. The intracellular portion of IA-2 (IA-2ic) was generated using the Pinpoint Vector (Promega, Madison, Wis.) which produces fusion proteins coupled at the N-terminus to a leader sequence biotinylated at a single lysine residue. This permitted purification using monomeric avidin columns, and also produced a biotinylated form of the antigen of interest for use in the Antigen Delivery System (ADS) (see below). The Pinpoint vector containing cDNA encoding IA-2ic was kindly provided by Dr. M. Christie, King's College London [Payton et al. (1995), J. Clin. Invest. 96:1506-1511]. The conditions for the purification of IA-2ic were as previously established [Payton et al. (1995), supra]. In brief, *E. coli* strain JM109 cells were transformed with the Pinpoint vector containing the IA-2ic cDNA. Colonies were subcultured onto minimal media/agarose plates and single colonies picked and cultured overnight at 37° C. with shaking in minimal media containing 2 μM d-biotin and 100 μg/ml ampicillin. Once the culture had attained an A$_{600}$ of 0.5, it was transferred (1:10 dilution) into LB medium containing 2 μM d-biotin and cultured at 37° C. with shaking for one hour. Protein expression was induced in the logarithmic phase of growth using 100 μM isopropyl β-D-thiogalactopyranoside (IPTG). Cells were harvested after 3-5 hours shaking at 37° C., by centrifuging at 8,000 g at 4° C. The cell pellet was resuspended in cell pellet buffer (CPB; 100 mM phosphate buffer, pH 7.2 containing 10 mM benzamidine and 1 mM phenylmethylsulfonylfluoride). Cells were then lysed on ice and soluble proteins released using a combination of lysozyme (1 mg/ml), Triton X-100 (0.1%) and deoxyribonuclease (200 U/ml) treatment. After removal of cell debris by centrifugation (14,000 g for 15 minutes at 4° C.), the biotinylated fusion protein was purified from the supernatant by passage, at a flow rate of 8 ml/hour, over an avidin-resin column (SoftLink, Promega, Madison, Wis.) prepared according to the manufacturer's instructions and equilibrated in CPB. After extensive column washing, the biotinylated fusion protein was eluted using an excess of 5 μM d-biotin, separated from free d-biotin using a G-25 column (Pharmacia), and concentrated 10- to 100-fold using an Amicon B15 concentrator with a 15 kDa molecular weight "cutoff." Purity, which was typically >90%, was assessed by SDS-PAGE and Western blot analysis in which avidin-peroxidase was used in the developing step.

GAD65 cDNA obtained from RNA extracted from human pancreatic islets was cloned into the pET 12 vector (Stratagene), in which expression is controlled by the T7 promotor downstream of a biotinylation tag sequence and a histidine purification tag designed based on the Pinpoint vector. This pET 12 vector system has the advantage that fusion protein expression can be induced in the protease deficient strain of *E. coli*, BLR (DE3) pLysS.

GAD65 was generated as follows. BLR (DE3) pLysS bacteria were transformed with the GAD65 cDNA containing vector and a colony picked into LB and grown at 37° C. with shaking at 225 rpm until an A$_{600}$ of 0.6-1.0 was reached. Cells were then resuspended in fresh LB, seeded at a dilution of 1:25, grown under the same conditions to an A$_{600}$ 0.4, and induced at 30° C. with 2 mM IPTG for 3 hours. A bacterial pellet obtained by centrifugation was resuspended in 8 M guanidine hydrochloride (GuHCl), 50 mM NaH$_2$PO$_4$, 10 mM Tris, 0.1% Triton X-100, 50 mM 2-mercaptoethanol (2-ME), pH 8.0; sonicated; and centrifuged for 1 hour at 4° C. at 40,000 g. The supernatant was dialyzed against a 10× excess of the 8M GuHCl buffer without 2-ME and then added to a 50% nickel resin slurry for 1 hour, rocking at room temperature. The nickel resin was resuspended in a column and washed with urea buffers provided by the manufacturers of the nickel resin (Qiagen, Germany) but supplemented with 5 mM 2-ME and 0.1% Triton X-100. Proteins were eluted using urea buffers of pH 5.9 and pH 4.5 and dialyzed against 4M urea, containing 50 μM pyridoxal phosphate, 20 mM sodium glutamate, 0.05% Triton X-100, 5 mM 2-ME and 2M L-arginine. The preparation was then dialyzed against sodium dodecylsulfate (SDS) (0.1%) gel running buffer containing 2.5 mM glutathione, 50 μM pyridoxal phosphate. Dialysis was repeated against an identical buffer containing a 10-fold lower concentration of SDS. Dialysis was then performed against a solution containing 4 mM hepes, 20 mM sodium glutamate, 50 μM pyridoxal phosphate, 2.5 mM glutathione. Final dialysis was against the same buffer without sodium glutamate. At this stage, the yellow, biotinylated GAD65 was stored at 4° C. or lyophilized.

Human pre-proinsulin cDNA was kindly provided by Dr. D. Steiner and has been cloned as described above for GAD65. Biotinylated pre-proinsulin was produced and purified under conditions similar to those for production and purification of GAD65.

Antigen delivery system (ADS). For the ADS, harvested and washed Priess cells were suspended at 5×10$^7$/ml in cold HBSS supplemented with b-PMW (300 ng/ml) and incubated on ice for 30 mins. After washing in HBSS, cells were resuspended at 5×10$^7$/ml in HBSS containing 0.5 mg/ml avidin and incubated on ice for 30 mins. After washing, the cells were resuspended in HBSS supplemented with 10-40 µg/ml biotinylated IA-2ic and incubated for 30 mins on ice. After washing, the cells were resuspended in pre-warmed RPMI 1640/10% FCS (1×10$^6$/ml) and cultured at 37° C. in 5% CO$_2$ for 6 hours. The cells were pelleted and stored at −80° C. until HLA molecule purification was performed.

HLA class II purification. DR4 molecule purification was carried out as previously described [Gorga et al. (1987), J. Biol. Chem. 262:16087-16094]. Cell pellets that had been obtained from the ADS and stored at −80° C. were thawed and homogenized in hypotonic buffer. A crude membrane fraction was prepared by high-speed centrifugation and solubilized in NP40. The detergent-soluble fraction was passed over a series of immunoaffinity columns containing Protein A-Sepharose or AffiGel 10 matrix material conjugated with monoclonal antibodies (mAb) that bind to MHC class I molecules (mAb W6/32), DR molecules (mAb LB3.1 or mAb L243), and DQ3 family molecules (mAb IVD12), respectively. Each of these mAbs recognizes the native dimer conformation of the HLA class I or class II molecules on cells of the indicated B lymphocyte lines. The immunoaffinity columns were eluted with 50 mM glycine, pH 11.5/0.1% sodium deoxycholate, and immediately neutralized and dialyzed against 10 mM Tris, pH 8.0/0.1% sodium deoxycholate. Protein purity was assessed by SDS-PAGE and quantitated by the BCA assay.

Peptide Analysis. All HLA class II protein samples were concentrated to 100 µl using an ultrafiltration device (Amicon Centricon 10) prior to peptide extraction. Naturally processed peptide repertoires were acid eluted from HLA class II molecules by adding 800 µl 10% acetic acid, and incubated for 15 minutes at 70° C., as described [Chicz et al. (1993), J. Exp. Med. 178:24-47]. The peptides were separated from the remaining HLA protein by ultrafiltration with the Centricon 10 device. The "flow-through" fraction containing the acid-extracted peptides was concentrated on a Savant SpeedVac to a volume of approximately 20-30 µl and stored at −80° C. The acid-extracted peptide mixtures were then separated by reverse phase chromatography as previously described [Chicz et al. (1993), supra], but with minor modifications. Briefly, the separations were carried out using a microbore C18 column (1.0×250 mm; Vydac, Hesperia, Calif.) with a flow rate of 50 µl/minute. The column effluent was split such that 2% was immediately loaded onto a matrix assisted laser desorption in-time-of-flight (MALDI-TOF) mass spectrometry sample plate, with the remaining 98% being collected for storage at −20° C. The samples were prepared for mass spectrometry analysis by adding 0.4 µL of matrix (α-cyano-4-hydroxycinnamic acid, 10 mg/ml in 50% acetonitrile/0.1% trifluoroacetic acid) and allowed to air dry. Mass spectra were collected at optimum laser intensities by averaging the ion signals from 128 individual scans in both linear and reflector modes using a single stage extended length reflector time-of-flight mass spectrometer (Voyager Elite XL; PerSeptive Biosystems, Framingham, Mass.). Time to mass conversion was performed by external calibration using synthetic peptides.

An automated microcapillary liquid chromatography-mass spectroscopy (LC-MS) approach with data dependent collision-assisted dissociation (CAD) for sequencing low levels of naturally processed HLA associated peptides was developed to directly sequence targeted peptide masses as determined by the MALDI-TOF-MS approach previously described. Peptide fractions separated by reversed phase chromatography are diluted to a final volume of 5-20 µl to aid handling and permit the use of second dimension reversed phase separations. The resultant peptide solution can then be preconcentrated by trapping peptides using a small bed (0.5-1.0 µL) of polymeric reversed phase support. This also facilitates removal of hydrophilic contaminants by washing the trap with an aqueous solution. Subsequently, peptides are back flushed from the trapping phase onto the microcapillary (with an inner diameter of 75 µm and packed with 5-15 cm of 1-7 µm 100-200 Å C$_{18}$ or non-porous material) and separation is developed using a non-linear gradient. A mobile phase flow rate of ~0.5 µL/min is achieved by splitting the flow from the pumps and using a balance column. Peptide detection is by µ-electrospray MS. The voltage necessary to drive the electrospray is applied at the head of the microcapillary column and peptides are electrosprayed into the mass analyzer directly as they elute from the capillary. CAD experiments are triggered in a data dependent mode, using ions that are more abundant than a user-set threshold. Dynamic exclusion is used to ensure maximum peptide coverage (i.e., minor responses are analyzed by CAD following a user determined number of CAD experiments of a single peptide response) by writing an exclusion list during assay progression so that a given ion will not be analyzed by multiple CAD experiments. The time that a given ion resides on the exclusion list is dependent upon the quality of the chromatographic separations. This must be determined experimentally. In this way, separated isobaric responses may be analyzed. Peptide sequencing sensitivity better than 1 fmol can be achieved using this method.

Epitope Verification (EV)

To establish that peptide epitopes identified are relevant to IDDM (i.e., that they are recognized by CD4+ T cells of patients with IDDM or pre-IDDM expressing the DR4 molecule but not by non-diabetic controls also expressing the DR4 molecule), T cell proliferation assays were carried out using synthetic peptides having amino acid sequences based upon the peptides identified by mass spectrometry to be derived from IA-2ic. Peptides were synthesized using Fmoc chemistry with an Applied Biosystems SYNERGY peptide synthesizer and purified by preparative RP-HPLC on a Waters 2690 Alliance system equipped with a Radial Compression Module. The amino acid sequences and purity of greater than 90% for all the synthetic peptides was confirmed by MALDI-MS and analytical HPLC. Peripheral blood mononuclear cells from recent onset IDDM patients (<6 months from diagnosis) and healthy controls expressing the appropriate HLA DR4 molecules were separated by density gradient centrifugation and co-cultured in wells of 96-well U-bottom plates with peptides at a concentration of 10 µg/ml for 5 days in 150 µl RPMI 1640/10% pooled normal AB serum, followed by pulsing with 0.5 µCi [$^3$H]-thymidine/well and harvesting onto filters for radioactivity counting measured in counts per minute (cpm). There were twelve replicate wells per test group. Results were expressed as a stimulation index (SI) which is the ratio of the cpm obtained from cultures containing peptide to the cpm obtained from cultures without peptide (mean cpm of 12 wells in each case). The data were also analyzed in terms of the fraction of "positive culture wells." A positive culture well was one that contained peptide and resulted in cpm>mean cpm+2SD obtained from cultures without peptide. T cell responses were considered significant when the SI is >2.0 and >40% wells are positive.

Binding Assay

Synthetic peptides with amino acid sequences based on the 6 core regions identified by the IMF were tested for their ability to bind to isolated HLA-DR4 molecules in a binding inhibition assay performed essentially as previously described [Chicz et al. (1997), J. Immunol. 159: 4935-4942]. In brief, aliquots of immunopurified preparation of HLA-DR4 (final concentration of 10 g/ml) were incubated with a biotinylated HLA-DR4 binding peptide (consisting of residues 98-117 of class II MHC invariant chain) ("the indicator peptide") (1 µM) and varying concentrations of the test peptides in 0.2 ml tubes. After an overnight incubation at room temperature, the contents of each tube were transferred to a well of a 96-well plastic microtiter plate precoated with anti-HLA-DR4 antibody. The microtiter plates were rocked for 60 min at room temperature and unbound material was removed by rigorous washing. The relative amount of bound standard peptide in each well was determined by measuring color development after addition of streptavidin-conjugated alkaline phosphatase, washing, and adding a chromogenic alkaline phosphatase substrate.

Example 1

Analysis of HLA DR4 binding Peptides Derived by Natural Processing of IA-2ic By B Lymphocytes To establish whether the described ADS leads to the generation of peptides (bound to HLA class II molecules on the surface) similar to those produced by APC following natural uptake of a parent polypeptide, a tetanus toxoid-(TT-) specific CD4+ T cell line (NG2) was generated. NG2 cells showed similar high levels of [$^3$H]-thymidine incorporation when co-cultured with APC in which biotinylated TT had been directed to the antigen processing organelles using the described ADS (mean cpm=7750 after 3 days of culture) as when cultured with normal APC and TT (mean cpm=8427). The background value obtained using APC without TT was 2528 cpm. After performing the ADS, aliquots of the Priess cells were incubated at 37° C. for 0, 1, 3, or 6 hours and then tested for the presence of TT on their surfaces by sequential treatment with rabbit anti-TT ("anti-TT") antiserum and FITC goat anti-rabbit Ig ("FARIG"), followed by flow cytometry analysis (FIG. 1). Compared with background samples treated with FARIG and not anti-TT (—), surface expression of TT was high at 0 hours (● ● ● ●), had diminished by 1 (-●-) and 3 (- - -) hours, and was completely absent by 6 hours (● ● ●). This experiment showed that proteins delivered via the ADS are internalized rapidly and are directed into the HLA class II antigen processing pathway, and that relevant peptide epitopes are presented to responsive CD4+ T lymphocytes.

The islet autoantigen IA-2ic was targeted onto the surface of Priess EBV-transformed B lymphocytes using the antigen delivery system (ADS) described above. In the first step, 5-10×10$^7$ Priess EBV transformed B cells were incubated with b-PWM. After washing away unbound b-PWM, avidin was added to the cell suspension to provide a bridge between the b-PWM and the b-IA-2ic.

Figure 2:
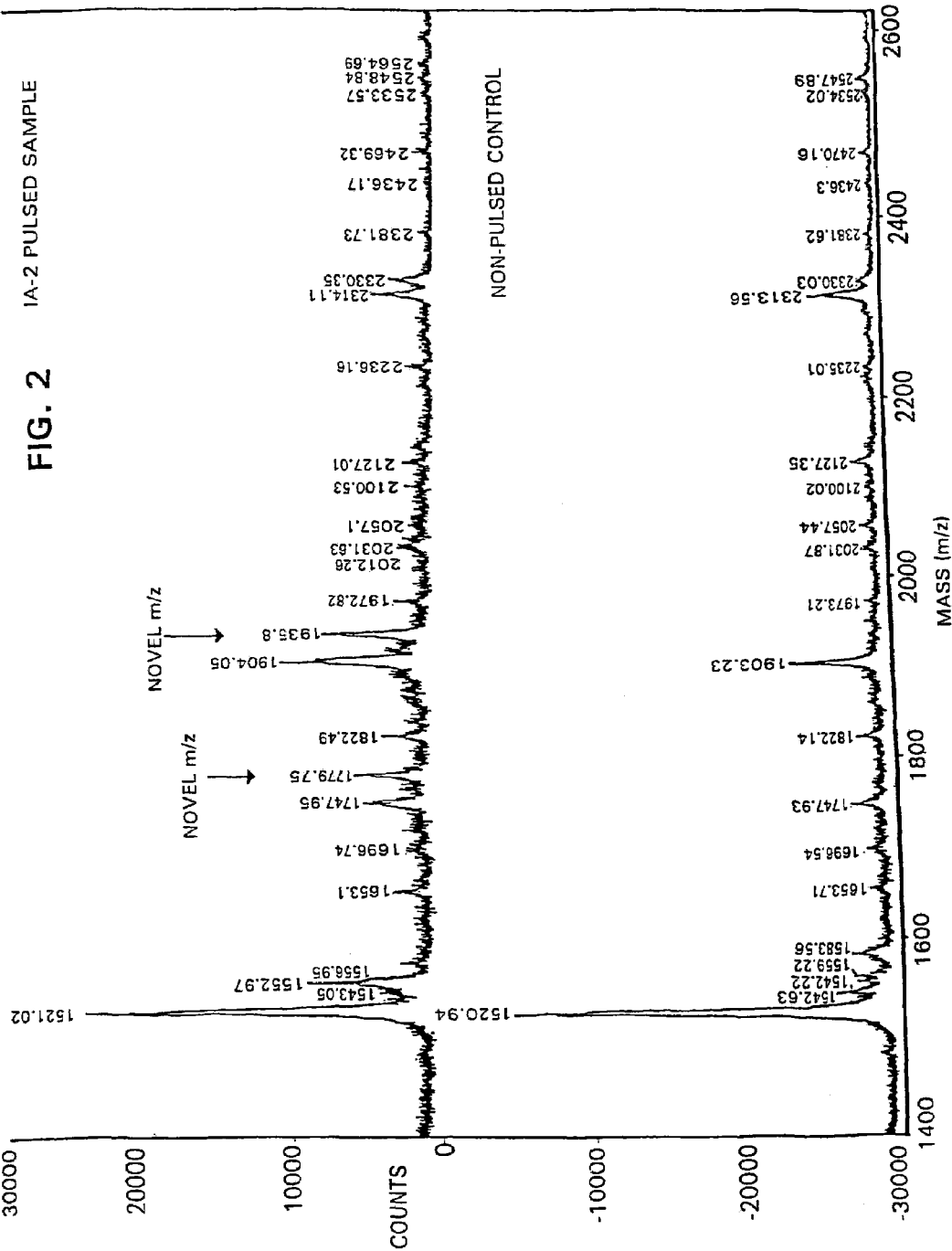
FIG. 2 is a diagram showing 2 appropriately aligned MALDI-TOF spectra derived from 2 mixtures of peptides obtained by IMF procedures in which separate aliquots of Priess cells were treated with either all the steps of the Immunological Mass Fingerprinting (IMF) procedure, including exposure to biotinylated IA-2ic, or all the steps of the IMF procedure, except exposure to biotinylated IA-2ic.

After pulsing with the biotinylated IA-2ic, the cells were incubated for 1-6 hours at 37° C. to allow internalization, processing and presentation. A control population of cells was pulsed with b-PWM and avidin only. HLA-DR4 (0401) molecules were purified from each cell pellet, bound peptides were eluted and separated by RP-HPLC, and each of 100 fractions was analyzed by MALDI-TOF. RP-HPLC analysis was highly reproducible, with chromatographic traces from the IA-2ic-pulsed and control HLA-DR4 preparations showing a similarity index of 96-99%. A subtractive approach was used to identify IA-2ic-derived peptides. Mass spectra of equivalent RP-HPLC fractions from biotinylated IA-2ic-pulsed and control preparations were overlaid and masses common to both were discounted from further analysis. An example of such a profile is shown in FIG. 2. The mass spectra for the HLA-DR4 (0401) peptide repertoire isolated from Priess cells pulsed with IA-2ic were compared to the spectra for the peptide repertoire isolated from control Priess cells to identify novel m/z (mass to charge ratio) values corresponding to peptides derived from IA-2ic (FIG. 2). In FIG. 2, while peaks with m/z values of about 1747 and 1822 were seen in the spectra obtained with peptide mixtures from both IA-2ic-pulsed and control Priess cells, peaks with m/z values of 1779.75 and 1935.8 were seen only in the spectrum obtained with the peptide mixture from IA-2ic pulsed Priess cells.

The experiment was performed in triplicate. Of the approximately 3000 m/z values observed, 85 novel masses were initially identified as potential naturally processed peptides from IA-2ic. Subsequent mass analyses using higher resolution and more stringent mass accuracy revealed 24 m/z values to have masses corresponding to candidate synthetic peptides derived from IA-2ic. These synthetic peptides were subjected to the mass spectrometry analysis. The mass identification was highly reproducible, with the same 24 masses being identified in three separate B cell preparations and 3 separate RP-HPLC separations. The same masses were seen when B cells were allowed to internalize, process and present antigen for 1 hour and 6 hours, although better peptide loading of DR4 molecules was seen at 1 hour. The sequences of the masses are shown in Table 1. Each of the sequences was a member of one of 6 nested sets of peptides. Nested sets are groups of peptides based around the same core region, but variably truncated or extended at the N- and C-termini. All 6 core regions contained amino acids known to be preferred for HLA-DR4 (0401) binding. The sequences of peptides with SEQ ID NO:10, SEQ ID NO:13, and SEQ ID NO:25 have been confirmed using the above-described CAD methodology applied to samples of the relevant MALDI-TOF separated material. Partial sequences corresponding to several peptides from each of the core regions previously described have also been obtained.

TABLE 1

Experimentally observed and calculated masses of IA-2 derived peptides eluted from HLA-DR4 (0401).

| Observed m/z | Calculated m/z | Residues | Corresponding IA-2ic sequence | Synthetic peptide used in Primary T cell assay |
|---|---|---|---|---|
| 1469.31 | 1468.65 | 657-671 | VSSQFSDAAQASPSS (SEQ ID NO: 1) | 654-674 |
| 1469.31 | 1468.65 | 656-670 | SVSSQFSDAAQASPS (SEQ ID NO: 2) | VSSVSSQFSDAAQASPSSHSS |
| 1469.31 | 1468.65 | 655-669 | SSVSSQFSDAAQASP (SEQ ID NO: 3) | (SEQ ID NO: 8) |
| 1866.76 | 1866.80 | 656-674 | SVSSQFSDAAQASPSSHSS (SEQ ID NO: 4) | |
| 2397.16 | 2397.08 | 652-675 | SRVSSVSSQFSDAAQASPSSHSST (SEQ ID NO: 5) | |

TABLE 1-continued

Experimentally observed and calculated masses of IA-2 derived peptides eluted from HLA-DR4 (0401).

| Observed m/z | Calculated m/z | Residues | Corresponding IA-2ic sequence | Synthetic peptide used in Primary T cell assay |
|---|---|---|---|---|
| 2441.48 | 2441.02 | 656-679 | SVSSQFSDAAQASPSSHSSTPSWC (SEQ ID NO: 6) | |
| 2485.29 | 2483.03 | 657-680 | VSSQFSDAAQASPSSHSSTPSWCE (SEQ ID NO: 7) | |
| 1367.44 | 1367.57 | 718-730 | AYQAEPNTCATAQ (SEQ ID NO: 17) | 709-732 |
| 1640.86 | 1640.68 | 716-731 | LCAYQAEPNTCATAQG (SEQ ID NO: 18) | LAKEWQALCAYQAEPNTCATAQGE |
| 1935.92 | 1935.91 | 709-725 | LAKEWQALCAYQAEPNT (SEQ ID NO: 19) | (SEQ ID NO: 22) |
| 1965.83 | 1965.88 | 718-736 | AYQAEPNTCATAQGEGNIK (SEQ ID NO: 20) | |
| 1968.75 | 1968.84 | 713-730 | WQALCAYQAEPNTCATAQ (SEQ ID NO: 21) | |
| 1489.64 | 1489.75 | 802-815 | GCTVIVMLTPLVED (SEQ ID NO: 23) | 797-817 |
| 1489.64 | 1489.75 | 803-816 | CTVIVMLTPLVEDG (SEQ ID NO: 24) | MVWESGCTVIVMLTPLVEDGV |
| 1762.88 | 1762.85 | 800-816 | ESGCTVIVMLTPLVEDG (SEQ ID NO: 25) | (SEQ ID NO: 32) |
| 1779.85 | 1780.19 | 797-812 | MVWESGCTVIVMLTPL (SEQ ID NO: 26) | |
| 1861.16 | 1860.97 | 801-818 | SGCTVIVMLTPLVEDGVK (SEQ ID NO: 27) | |
| 1861.16 | 1860.97 | 800-817 | ESGCTVIVMLTPLVEDGV (SEQ ID NO: 28) | |
| 1883.44 | 1882.88 | 795-810 | WQMVWESGCTVIVMLT (SEQ ID NO: 29) | |
| 2144.95 | 2144.97 | 793-810 | DFWQMVWESGCTVIVMLT (SEQ ID NO: 30) | |
| 2341.17 | 2339.15 | 794-813 | FWQMVWESGCTVIVMLTPLV (SEQ ID NO: 31) | |
| 1508.65 | 1508.74 | 861-872 | TQETRTLTQFHF (SEQ ID NO: 9) | 854-872 |
| 1539.34 | 1593.85 | 855-867 | YLKNVQTQETRTL (SEQ ID NO: 10) | FYLKNVQTQETRTLTQFHF |
| 1735.78 | 1735.87 | 859-872 | VQTQETRTLTQFHF (SEQ ID NO: 11) | (SEQ ID NO: 16) |
| 1806.79 | 1806.96 | 856-870 | LKNVQTQETRTLTQF (SEQ ID NO: 12) | |
| 1822.41 | 1822.96 | 855-869 | YLKNVQTQETRTLTQ (SEQ ID NO: 13) | |
| 1831.87 | 1830.94 | 857-871 | KNVQTQETRTLTQFH (SEQ ID NO: 14) | |
| 2341.17 | 2341.19 | 853-871 | SFYLKNVQTQETRTLTQFH (SEQ ID NO: 15) | |
| 1469.31 | 1469.67 | 957-969 | DQFEFALTAVAEE (SEQ ID NO: 33) | 955-975 |
| 1866.76 | 1866.90 | 957-973 | DQFEFALTAVAEEVNAI (SEQ ID NO: 34) | SKDQFEFALTAVAEEVNAILK |
| 1935.49 | 1936.04 | 959-976 | FEFALTAVAEEVNAILKA (SEQ ID NO: 35) | (SEQ ID NO: 37) |
| 1968.75 | 1968.95 | 955-972 | SKDQFEFALTAVAEEVNA (SEQ ID NO: 36) | |
| 1367.44 | 1367.67 | 754-765 | KVESSPSRSDYI (SEQ ID NO: 38) | 753-771 |
| 1367.44 | 1367.67 | 753-764 | LKVESSPSRSDY (SEQ ID NO: 39) | LKVESSPSRSDYINASPII |
| 1880.98 | 1880.96 | 752-768 | KLKVESSPSRSDYINAS (SEQ ID NO: 40) | (SEQ ID NO: 42) |
| 2441.48 | 2441.19 | 754-775 | KVESSPSRSDYINASPIIEHDP (SEQ ID NO: 41) LKVESSPSRSDYINASPII (SEQ ID NO: 42) | |

Six synthetic peptides with amino acid sequences based on the 6 core regions of IA-2ic were used to examine peripheral blood T cell responses in IDDM patients (expressing and not expressing HLA-DR4) and in healthy control subjects expressing HLA-DR4 (Table 2). Of 13 HLA-DR4 IDDM patients, 9 had T cells that showed significant ("POS" in Table 2) proliferative responses to at least one of the 6 peptides. Eleven of the DR4 patients expressed the 0401 allele and two expressed both the 0403 and 0405 alleles. The 0401, 0403, and 0405 genes encode similar DRβ chains, differing only at positions 57 (0405 S for D), 71 (0403 and 0405 R for K), 74 (0403 E for A) and 86 (0403 V for G) [Marsh, S. G., Tissue Antigens 51:467-507, (1998)]. The peptide binding motifs of these HLA-DR4 types are known and are similar, and all are predicted to bind to the 6 IA-2ic core peptide regions. T cells from only ⅛ non-DR4 IDDM patients proliferated when exposed to any of the peptides, and none of those from the control subjects (all 0401) responded to any of the peptides.

Peptides from all 6 of the 6 core regions elicited T cell responses, and T cells from most responder patients proliferated to a single peptide.

In toto, these data indicate that IMF method applied to the analysis of peptides produced by natural processing of IA-2ic resulted in the characterization of peptides that are recognized by CD4+ T lymphocytes specifically from HLA DR4 expressing IDDM patients and thus may be implicated in the IDDM disease process. This finding represents a significant advance in knowledge regarding the aetiology of IDDM and provides the basis for the development of therapeutic and/or prophylactic agents for IDDM, e.g., APL. It is expected that analogous methodologies can be similarly successful in identifying peptides involved in the CD4+ T lymphocyte-mediated pathogenesis of other diseases (see above) in which susceptibility is linked to the expression of a particular class II MHC molecule.

TABLE 2

Responses of T cells from patients with IDDM and control subjects to eluted IA-2 peptides

| Case | Age (years) | Duration (weeks) | DRB1 genotype | IA-2 auto-antibodies | T cell response to IA-2 peptide ||||| 
|---|---|---|---|---|---|---|---|---|---|
| | | | | | 654-674 | 709-732 | 955-975 | 797-817 | 854-872 |
| HLA-DR4 IDDM patients ||||||||||
| S (G) | 17 | 8 | 0401, 0101 | + | | | | POS | |
| G (G) | 26 | 12 | 0401, 1302 | + | POS | | | | |
| K (G) | 28 | 28 | 0401, 1101 | + | POS | | | | |
| ML | 29 | 3 | 0401, 0403 | − | | | | | POS |

TABLE 2-continued

Responses of T cells from patients with IDDM and control subjects to eluted IA-2 peptides

| Case | Age (years) | Duration (weeks) | DRB1 genotype | IA-2 auto-antibodies | T cell response to IA-2 peptide ||||| 
|---|---|---|---|---|---|---|---|---|---|
| | | | | | 654-674 | 709-732 | 955-975 | 797-817 | 854-872 |
| EW(B) | 29 | 16 | 0401/0401 | + | | | | POS | |
| RW(B) | 20 | 4 | 0401/0401 | + | POS | | | | |
| TH(B) | 19 | 4 | 0401/0301 | − | | | POS | | |
| DC (I) | 6 | 4 | 0403, 0405 | + | | POS | | | |
| GR | 13 | <1 | 0403, 0405 | + | POS | | | POS | POS |
| NC (B) | 36 | 16 | 0401/0404 | + | | | | | |
| HW | 15 | 12 | 0401/0401 | | | | | | |
| LG(G) | 16 | 4 | 0401, 0301 | + | | | | | |
| RM | 24 | 1 | 0401, 1302 | | | | | | |
| IDDM patients (non-DR4) ||||||||||
| JD | 28 | 4 | 0102, 0301 | − | POS | | | POS | POS |
| PQ | 20 | 25 | 0301 | − | | | | | |
| MI | 16 | 12 | 1201, 1301 | + | | | | | |
| ML (I) | 10 | 12 | 0101, 1101 | − | | | | | |
| ST (I) | 13 | 2 | 0301, 1301 | + | | | | | |
| OA | 23 | 1 | 1101, 1301 | − | | | | | |
| RM | 24 | 25 | 0301, 0901 | − | | | | | |
| JH(B) | 33 | 20 | 0301/08 | − | | | | | |
| HLA-DR4 Controls ||||||||||
| TL(G) | 36 | — | 0401, 0101 | − | | | | | |
| JB | 17 | — | 0401/0101 | − | | | | | |
| B(G) | 30 | — | 0401, 1302 | − | | | | | |
| MR | 24 | — | 0401, 1501 | − | | | | | |
| PH | 40 | — | 0401, 14 | − | | | | | |
| VB | 16 | — | 0401, 0403 | − | | | | | |
| AZ | 24 | — | 0401, 02 | − | | | | | |
| CF(G) | 30 | — | 0401, 0701 | − | | | | | |

Example 2

Binding of Consensus Peptides to Isolated HLA-DR4 Molecules

Figure 3:
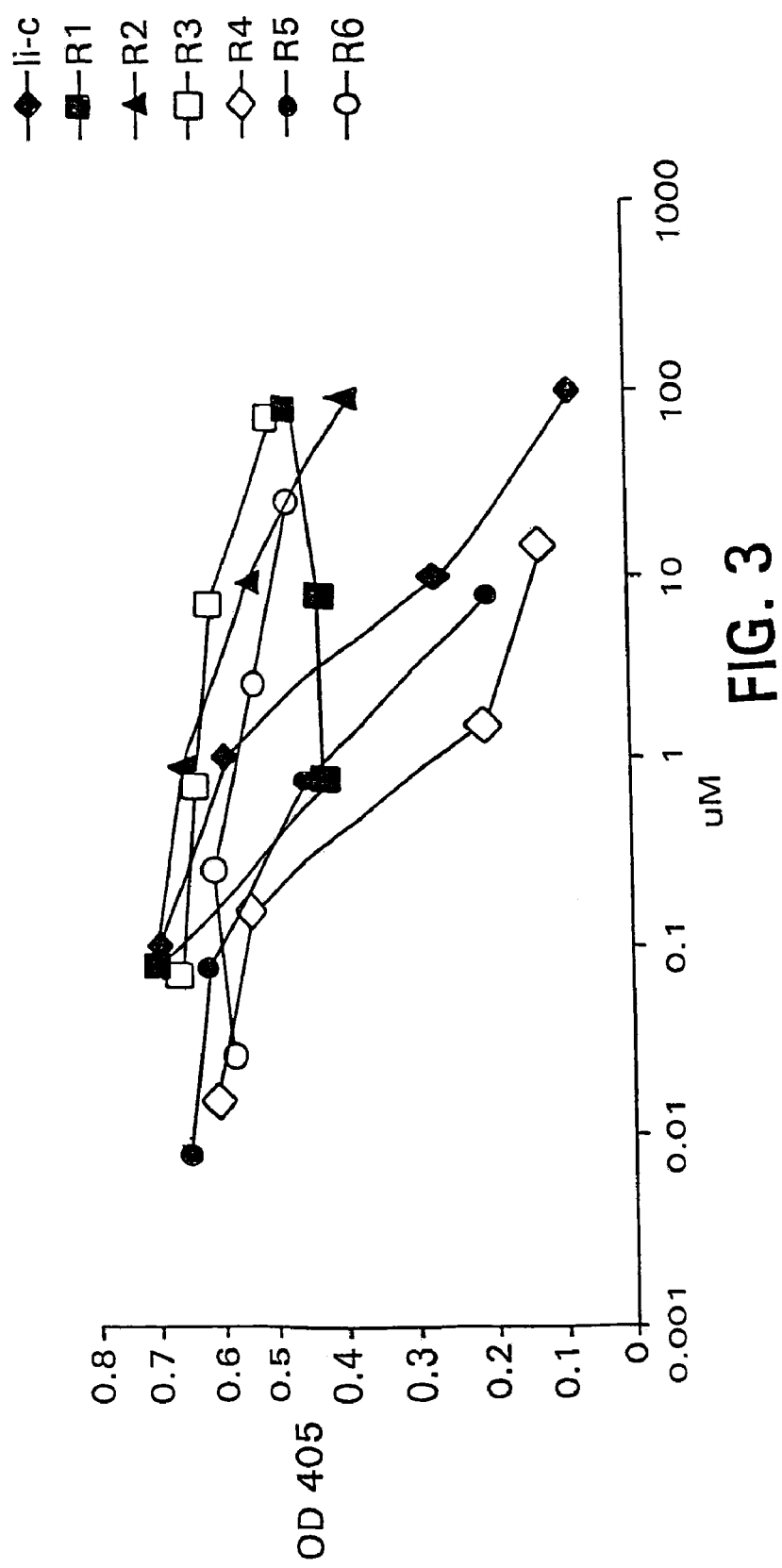
FIG. 3 is a series of line graphs showing the relative ability of 6 peptides (with amino acid sequences based on the 6 core regions of IA-2 identified by IMF) to inhibit binding of an invariant chain (Ii) peptide to isolated HLA DR4 molecules.

In order to test for the ability of the 6 consensus peptides representing the 6 core regions defined by the IMF described in Example 1, a binding inhibition assay was performed (FIG. 3). R1 was the peptide consisting of residues 797-817 of IA-2; R2 was the peptide consisting of residues 854-872 of IA-2; R3 was the peptide consisting of residues 753-771 of IA-2; R4 was the peptide consisting of residues 654-674 of IA-2; R5 was the peptide consisting of residues 709-732 of IA-2; R6 was the peptide consisting of residues 955-975 of IA-2; and Ii-c was the same as the indicator peptide (i.e., a peptide consisting of residues 98-117 of class II MHC invariant chain). The data presented in FIG. 3 indicate that: R4 and R5 bind strongly to HLA-DR4 molecules; Ii-c, R1, and R6 bind with intermediate avidity; and R2 and R3 bind weakly. These findings confirm that, as predicted by the IMF and EV procedures described in Example 1, the six consensus peptides (R1, R2, R3, and R4-R6) all bind to DR4 molecules. Thus, this type of binding assay or others known in the art (e.g., direct binding rather than binding inhibition assays) can be used as additional or substitute EV procedures to that described in Example 1.

Although the invention has been described with reference to the presently preferred embodiment, it should be understood that various modifications can be made without departing from the spirit of the invention. Accordingly, the invention is limited only by the following claims.

What is claimed is:

1. An isolated peptide that is less than 26 amino acid residues in length and binds to HLA-DR4, comprising a sequence AYQAEPNT (SEQ IID NO:49).

2. The isolated peptide of claim 1, consisting of the amino acid sequence AYQAEPNTCATAQ (SEQ ID NO:17).

3. The isolated peptide of claim 1, consisting of the amino acid sequence LCAYQAEPNTCATAQG (SEQ ID NO:18).

4. The isolated peptide of claim 1, consisting of the amino acid sequence LAKEWQALCAYQAEPNT (SEQ ID NO:19).

5. The isolated peptide of claim 1, consisting of the amino acid sequence AYQAEPNTCATAQGEGNIK (SEQ ID NO:20).

6. The isolated peptide of claim 1, consisting of the amino acid sequence WQALCAYQAEPNTCATAQ (SEQ ID NO:21).

7. The isolated peptide of claim 1, consisting of the amino acid sequence LAKEWQALCAYQAEPNTCATAQGE (SEQ ID NO:22).

* * * * *